US005837538A

United States Patent [19]
Scott et al.

[11] Patent Number: 5,837,538
[45] Date of Patent: Nov. 17, 1998

[54] PATCHED GENES AND THEIR USE

[75] Inventors: Matthew P Scott, Stanford; Lisa V. Goodrich, Palo Alto; Ronald L. Johnson, Redwood City, all of Calif.

[73] Assignee: Trustees of Leland Stanford, Jr. University, Stanford, Calif.

[21] Appl. No.: 540,406

[22] Filed: Oct. 6, 1995

Related U.S. Application Data

[63] Continuation-in-part of Ser. No. 319,745, Oct. 7, 1994, abandoned.
[51] Int. Cl.$^6$ .............................. C12N 5/16; C12N 15/11; C12N 15/09
[52] U.S. Cl. ........................ 435/325; 536/23.1; 536/23.5; 536/24.31; 435/172.3; 435/69.1; 435/320.1; 435/91.2; 424/93.21
[58] Field of Search .................................. 536/23.1, 23.5, 536/24.31; 435/172.3, 69.1, 325, 91.2, 320.1; 424/93.21

[56] References Cited

PUBLICATIONS

Chavrier et al., Gene, vol. 112, pp. 261–264, 1992.
Ma et al., Biochemistry, vol. 31, pp. 10922–10928, 1992.
Thummel et al., Gene, vol. 74, pp. 445–456, 1988.
J.E, Hooper, et al., "The Drosophila Patched Gene Encodes a Putative Membrane Protein Required For Segmental Patterning", Cell (1989), 59:751–765.
A.J. Forbes, et al., "Genetic Analysis of Hedgehog Signalling in The Drosophila Embryo", Development 1993 Supplement (1993), 115–124.
P.W. Ingham, "Hedgehog Points The Way", Current Biology (1994), Vo. 4, No. 4.
H. Roelink, et al., "Floor Plate and Motor Neuron Induction by vhh–1, A Vertebrate Homolog of Hedgehog Expressed By The Notochord", Cell (1994), 76:761–775.
J. Heemskerk, et al., "Drosophila Hedgehog Acts as a Morphogen in Cellular Patterning", Cell (1994), 76:449–460.
T. Tabata, et al., "Hedgehog is a Signaling Protein with a Key Role in patterning Drosophila Imaginal Discs", Cell (1994), 76:89–102.

S. Krauff, et al., "A Functionally Conserved Homolog of The Drosophila Segment Polarity Gene hh is Expressed in Tissues with Polarizing Activity in Zebrafish Embryos", Cell (1993), 75:1431–1444.
Y. Echelard, et al. "Sonic Hedgehog, A Member of a Family of Putative Signaling Molecules, is Implicated in The Regulation of CNS Polarity", Cell (1993), 75:1417–1430.
R.D. Riddle, et al., "Sonic Hedgehog Mediates The Polarizing Acitivity of The ZPA", Cell (1993), 75:1401–1416.
P.W. Ingham, et al., "Role of The Drosophila Patched Gene in Positional Signalling", Nature (1991), 353:184–187.
Y. Nakano, et al., "A Protein With Several Possible Membrane–Spanning Domains Encoded by the Drosophila Segment Polarity Gene Patched", Nature (1989), 341:508–513.
A.A. Simcox, et al., "Imaginal Discs can be Recovered From Cultured Embryos Mutant For the Segment–Polarity Genes Engrailed, Naked and Patched but not From Wingless", Development 107 (1989), 715–722.
A. Hidalgo, et al., "Cell Patterning in the Drosophila Segment: Spatial Regulation of The Segment Polarity Gene Patched", Development 110 (1990, 291–301.
R.G. Phillips, et al., "The Drosophila Segment Polarity Gene Patched is Involved in a Position–Signalling Mechanism in Imaginal Discs", Development 110 (1990), 105–114.
A.M. Taylor, et al., "Contrasting Distributions of Patched and Hedgehog Proteins in the Drosophila Embryo", Mechanism of Develop. (1993), 42:89–96.
J. Sampedro, et al., "Unrestricted Expression of the Drosophila Gene Patched Allows a Normal Segment Polarity", Nature (1993), 353:187–190.

*Primary Examiner*—Jasemine C. Chambers
*Assistant Examiner*—Jill D. Schmuck
*Attorney, Agent, or Firm*—Matthew P. Vincent; Beth E. Arnold; Foley, Hoag & Eliot, LLP

[57] ABSTRACT

Invertebrate and vertebrate patched genes are provided, including the mouse and human patched genes, as well as methods for isolation of related genes, where the genes may be of different species or in the same family. Having the ability to regulate the expression of the patched gene, allows for the elucidation of embryonic development, cellular regulation associated with signal transduction by the patched gene, the identification of agonist and antagonist to signal transduction, identification of ligands for binding to patched, isolation of the ligands, and assaying for levels of transcription and expression of the patched gene.

32 Claims, 1 Drawing Sheet

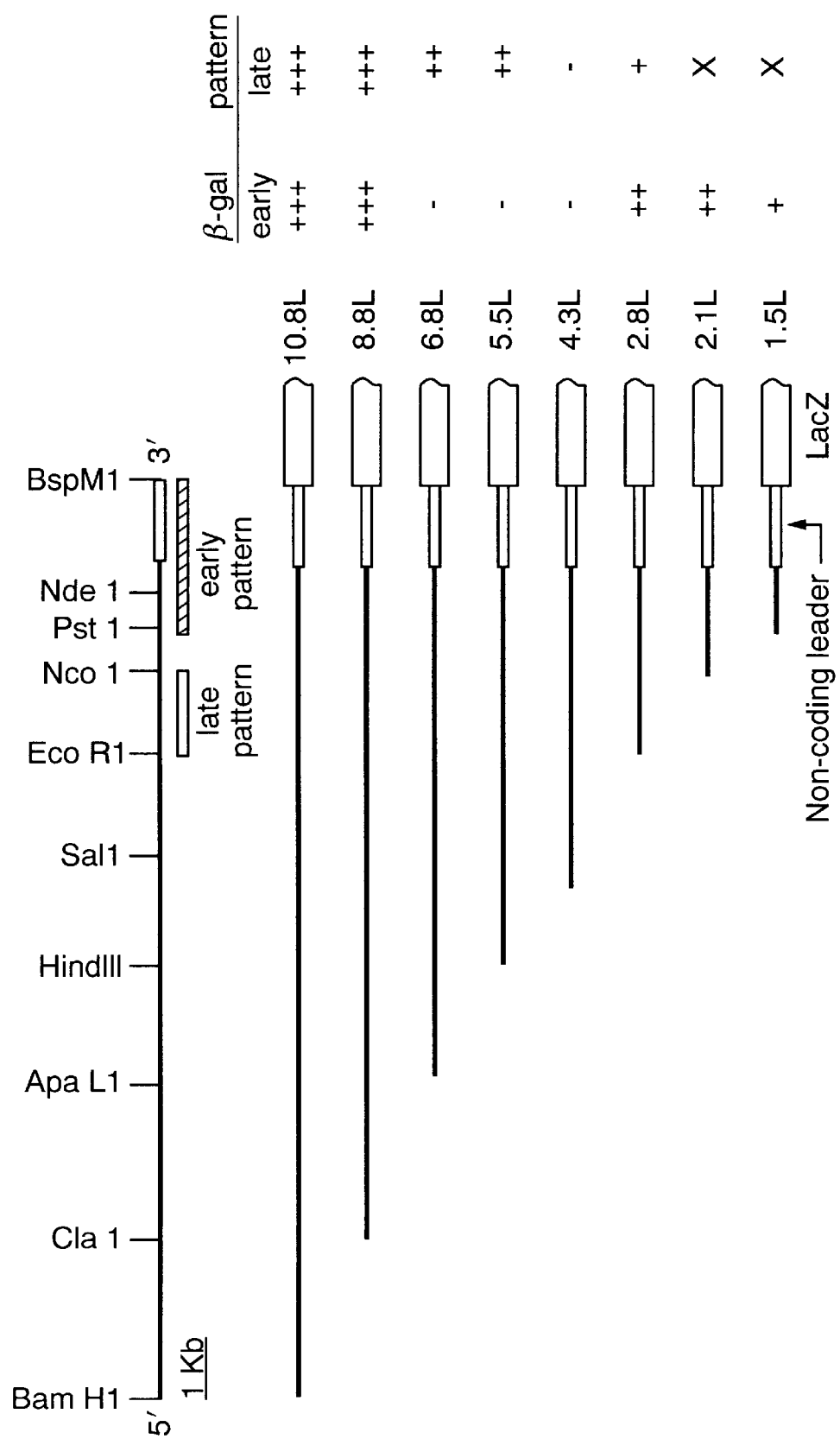

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 736 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AACNNCNNTN  NATGGCACCC  CCNCCCAACC  TTTNNNCCNN  NTAANCAAAA  NNCCCCNTTT      60
NATACCCCCT  NTAANANTTT  TCCACCNNNC  NNAAANNCCN  CTGNANACNA  NGNAAANCCN     120
TTTTTNAACC  CCCCCCACCC  GGAATTCCNA  NTNNCCNCCC  CCAAATTACA  ACTCCAGNCC     180
AAAATTNANA  NAATTGGTCC  TAACCTAACC  NATNGTTGTT  ACGGTTTCCC  CCCCCAAATA     240
CATGCACTGG  CCCGAACACT  TGATCGTTGC  CGTTCCAATA  AGAATAAATC  TGGTCATATT     300
AAACAAGCCN  AAAGCTTTAC  AAACTGTTGT  ACAATTAATG  GGCGAACACG  AACTGTTCGA     360
ATTCTGGTCT  GGACATTACA  AAGTGCACCA  CATCGGATGG  AACCAGGAGA  AGGCCACAAC     420
CGTACTGAAC  GCCTGGCAGA  AGAAGTTCGC  ACAGGTTGGT  GGTTGGCGCA  AGGAGTAGAG     480
TGAATGGTGG  TAATTTTTGG  TTGTTCCAGG  AGGTGGATCG  TCTGACGAAG  AGCAAGAAGT     540
CGTCGAATTA  CATCTTCGTG  ACGTTCTCCA  CCGCCAATTT  GAACAAGATG  TTGAAGGAGG     600
CGTCGAANAC  GGACGTGGTG  AAGCTGGGGG  TGGTGCTGGG  GGTGGCGGCG  GTGTACGGGT     660
GGGTGGCCCA  GTCGGGGCTG  GCTGCCTTGG  GAGTGCTGGT  CTTNGCGNGC  TNCNATTCGC     720
CCTATAGTNA  GNCGTA                                                         736
```

( 2 ) INFORMATION FOR SEQ ID NO:2:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Xaa  Pro  Pro  Pro  Asn  Tyr  Asn  Ser  Xaa  Pro  Lys  Xaa  Xaa  Xaa  Leu  Val
  1                    5                    10                       15
Leu  Thr  Pro  Xaa  Val  Val  Thr  Val  Ser  Pro  Pro  Lys  Tyr  Met  His  Trp
               20                   25                        30
Pro  Glu  His  Leu  Ile  Val  Ala  Val  Pro  Ile  Arg  Ile  Asn  Leu  Val  Ile
          35                        40                   45
Leu  Asn  Lys  Pro  Lys  Ala  Leu  Gln  Thr  Val  Val  Gln  Leu  Met  Gly  Glu
     50                       55                        60
His  Glu  Leu  Phe  Glu  Phe  Trp  Ser  Gly  His  Tyr  Lys  Val  His  His  Ile
65                        70                   75                            80
```

```
            Gly  Trp  Asn  Gln  Glu  Lys  Ala  Thr  Thr  Val  Leu  Asn  Ala  Trp  Gln  Lys
                            85                      90                       95

Lys  Phe  Ala  Gln  Val  Gly  Gly  Trp  Arg  Lys  Glu
                           100                      105
```

( 2 ) INFORMATION FOR SEQ ID NO:3:

( i ) SEQUENCE CHARACTERISTICS:
        ( A ) LENGTH: 5187 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
GGGTCTGTCA   CCCGGAGCCG   GAGTCCCCGG   CGGCCAGCAG   CGTCCTCGCG   AGCCGAGCGC       60
CCAGGCGCGC   CCGGAGCCCG   CGGCGGCGGC   GGCAACATGG   CCTCGGCTGG   TAACGCCGCC      120
GGGGCCCTGG   GCAGGCAGGC   CGGCGGCGGG   AGGCGCAGAC   GGACCGGGGG   ACCGCACCGC      180
GCCGCGCCGG   ACCGGGACTA   TCTGCACCGG   CCCAGCTACT   GCGACGCCGC   CTTCGCTCTG      240
GAGCAGATTT   CCAAGGGGAA   GGCTACTGGC   CGGAAAGCGC   CGCTGTGGCT   GAGAGCGAAG      300
TTTCAGAGAC   TCTTATTTAA   ACTGGGTTGT   TACATTCAAA   GAACTGCGG   CAAGTTTTTG      360
GTTGTGGGTC   TCCTCATATT   TGGGGCCTTC   GCTGTGGGAT   TAAAGGCAGC   TAATCTCGAG      420
ACCAACGTGG   AGGAGCTGTG   GGTGGAAGTT   GGTGGACGAG   TGAGTCGAGA   ATTAAATTAT      480
ACCCGTCAGA   AGATAGGAGA   AGAGGCTATG   TTTAATCCTC   AACTCATGAT   ACAGACTCCA      540
AAAGAAGAAG   GCGCTAATGT   TCTGACCACA   GAGGCTCTCC   TGCAACACCT   GGACTCAGCA      600
CTCCAGGCCA   GTCGTGTGCA   CGTCTACATG   TATAACAGGC   AATGGAAGTT   GGAACATTTG      660
TGCTACAAAT   CAGGGGAACT   TATCACGGAG   ACAGGTTACA   TGGATCAGAT   AATAGAATAC      720
CTTTACCCTT   GCTTAATCAT   TACACCTTTG   GACTGCTTCT   GGGAAGGGGC   AAAGCTACAG      780
TCCGGGACAG   CATACCTCCT   AGGTAAGCCT   CCTTTACGGT   GGACAAACTT   TGACCCCTTG      840
GAATTCCTAG   AAGAGTTAAA   GAAAATAAAC   TACCAAGTGG   ACAGCTGGGA   GGAAATGCTG      900
AATAAAGCCG   AAGTTGGCCA   TGGGTACATG   GACCGGCCTT   GCCTCAACCC   AGCCGACCCA      960
GATTGCCCTG   CCACAGCCCC   TAACAAAAAT   TCAACCAAAC   CTCTTGATGT   GGCCCTTGTT     1020
TTGAATGGTG   GATGTCAAGG   TTTATCCAGG   AAGTATATGC   ATTGGCAGGA   GGAGTTGATT     1080
GTGGGTGGTA   CCGTCAAGAA   TGCCACTGGA   AAACTTGTCA   GCGCTCACGC   CCTGCAAACC     1140
ATGTTCCAGT   TAATGACTCC   CAAGCAAATG   TATGAACACT   TCAGGGCTA   CGACTATGTC     1200
TCTCACATCA   ACTGGAATGA   AGACAGGGCA   GCCGCCATCC   TGGAGGCCTG   GCAGAGGACT     1260
TACGTGGAGG   TGGTTCATCA   AAGTGTCGCC   CCAAACTCCA   CTCAAAAGGT   GCTTCCCTTC     1320
ACAACCACGA   CCCTGGACGA   CATCCTAAAA   TCCTTCTCTG   ATGTCAGTGT   CATCCGAGTG     1380
GCCAGCGGCT   ACCTACTGAT   GCTTGCCTAT   GCCTGTTTAA   CCATGCTGCG   CTGGGACTGC     1440
TCCAAGTCCC   AGGGTGCCGT   GGGGCTGGCT   GGCGTCCTGT   TGGTTGCGCT   GTCAGTGGCT     1500
GCAGGATTGG   GCCTCTGCTC   CTTGATTGGC   ATTTCTTTTA   ATGCTGCGAC   AACTCAGGTT     1560
TTGCCGTTTC   TTGCTCTTGG   TGTTGGTGTG   GATGATGTCT   TCCTCCTGGC   CCATGCATTC     1620
AGTGAAACAG   GACAGAATAA   GAGGATTCCA   TTTGAGGACA   GGACTGGGGA   GTGCCTCAAG     1680
CGCACCGGAG   CCAGCGTGGC   CCTCACCTCC   ATCAGCAATG   TCACCGCCTT   CTTCATGGCC     1740
GCATTGATCC   CTATCCCTGC   CCTGCGAGCG   TTCTCCCTCC   AGGCTGCTGT   GGTGGTGGTA     1800
```

| | | | | | | |
|---|---|---|---|---|---|---|
| TTCAATTTTG | CTATGGTTCT | GCTCATTTTT | CCTGCAATTC | TCAGCATGGA | TTTATACAGA | 1860 |
| CGTGAGGACA | GAAGATTGGA | TATTTTCTGC | TGTTTCACAA | GCCCCTGTGT | CAGCAGGGTG | 1920 |
| ATTCAAGTTG | AGCCACAGGC | CTACACAGAG | CCTCACAGTA | ACACCCGGTA | CAGCCCCCA | 1980 |
| CCCCCATACA | CCAGCCACAG | CTTCGCCCAC | GAAACCCATA | TCACTATGCA | GTCCACCGTT | 2040 |
| CAGCTCCGCA | CAGAGTATGA | CCCTCACACG | CACGTGTACT | ACACCACCGC | CGAGCCACGC | 2100 |
| TCTGAGATCT | CTGTACAGCC | TGTTACCGTC | ACCCAGGACA | ACCTCAGCTG | TCAGAGTCCC | 2160 |
| GAGAGCACCA | GCTCTACCAG | GGACCTGCTC | TCCCAGTTCT | CAGACTCCAG | CCTCCACTGC | 2220 |
| CTCGAGCCCC | CCTGCACCAA | GTGGACACTC | TCTTCGTTTG | CAGAGAAGCA | CTATGCTCCT | 2280 |
| TTCCTCCTGA | AACCCAAAGC | CAAGGTTGTG | GTAATCCTTC | TTTTCCTGGG | CTTGCTGGGG | 2340 |
| GTCAGCCTTT | ATGGGACCAC | CCGAGTGAGA | GACGGGCTGG | ACCTCACGGA | CATTGTTCCC | 2400 |
| CGGGAAACCA | GAGAATATGA | CTTCATAGCT | GCCCAGTTCA | AGTACTTCTC | TTTCTACAAC | 2460 |
| ATGTATATAG | TCACCCAGAA | AGCAGACTAC | CCGAATATCC | AGCACCTACT | TTACGACCTT | 2520 |
| CATAAGAGTT | TCAGCAATGT | GAAGTATGTC | ATGCTGGAGG | AGAACAAGCA | ACTTCCCCAA | 2580 |
| ATGTGGCTGC | ACTACTTTAG | AGACTGGCTT | CAAGGACTTC | AGGATGCATT | TGACAGTGAC | 2640 |
| TGGGAAACTG | GGAGGATCAT | GCCAAACAAT | TATAAAAATG | GATCAGATGA | CGGGGTCCTC | 2700 |
| GCTTACAAAC | TCCTGGTGCA | GACTGGCAGC | CGAGACAAGC | CCATCGACAT | TAGTCAGTTG | 2760 |
| ACTAAACAGC | GTCTGGTAGA | CGCAGATGGC | ATCATTAATC | CGAGCGCTTT | CTACATCTAC | 2820 |
| CTGACCGCTT | GGGTCAGCAA | CGACCCTGTA | GCTTACGCTG | CCTCCCAGGC | CAACATCCGG | 2880 |
| CCTCACCGGC | CGGAGTGGGT | CCATGACAAA | GCCGACTACA | TGCCAGAGAC | CAGGCTGAGA | 2940 |
| ATCCAGCAG | CAGAGCCCAT | CGAGTACGCT | CAGTTCCCTT | TCTACCTCAA | CGGCCTACGA | 3000 |
| GACACCTCAG | ACTTTGTGGA | AGCCATAGAA | AAAGTGAGAG | TCATCTGTAA | CAACTATACG | 3060 |
| AGCCTGGGAC | TGTCCAGCTA | CCCCAATGGC | TACCCCTTCC | TGTTCTGGGA | GCAATACATC | 3120 |
| AGCCTGCGCC | ACTGGCTGCT | GCTATCCATC | AGCGTGGTGC | TGGCCTGCAC | GTTTCTAGTG | 3180 |
| TGCGCAGTCT | TCCTCCTGAA | CCCCTGGACG | GCCGGGATCA | TTGTCATGGT | CCTGGCTCTG | 3240 |
| ATGACCGTTG | AGCTCTTTGG | CATGATGGGC | CTCATTGGGA | TCAAGCTGAG | TGCTGTGCCT | 3300 |
| GTGGTCATCC | TGATTGCATC | TGTTGGCATC | GGAGTGGAGT | TCACCGTCCA | CGTGGCTTTG | 3360 |
| GCCTTTCTGA | CAGCCATTGG | GGACAAGAAC | CACAGGGCTA | TGCTCGCTCT | GGAACACATG | 3420 |
| TTTGCTCCCG | TTCTGGACGG | TGCTGTGTCC | ACTCTGCTGG | GTGTACTGAT | GCTTGCAGGG | 3480 |
| TCCGAATTTG | ATTTCATTGT | CAGATACTTC | TTTGCCGTCC | TGGCCATTCT | CACCGTCTTG | 3540 |
| GGGGTTCTCA | ATGGACTGGT | TCTGCTGCCT | GTCCTCTTAT | CCTTCTTTGG | ACCGTGTCCT | 3600 |
| GAGGTGTCTC | CAGCCAATGG | CCTAAACCGA | CTGCCCACTC | CTTCGCCTGA | GCCGCCTCCA | 3660 |
| AGTGTCGTCC | GGTTTGCCGT | GCCTCCTGGT | CACACGAACA | ATGGGTCTGA | TTCCTCCGAC | 3720 |
| TCGGAGTACA | GCTCTCAGAC | CACGGTGTCT | GGCATCAGTG | AGGAGCTCAG | GCAATACGAA | 3780 |
| GCACAGCAGG | GTGCCGGAGG | CCCTGCCCAC | CAAGTGATTG | TGGAAGCCAC | AGAAAACCCT | 3840 |
| GTCTTTGCCC | GGTCCACTGT | GGTCCATCCG | GACTCCAGAC | ATCAGCCTCC | CTTGACCCCT | 3900 |
| CGGCAACAGC | CCCACCTGGA | CTCTGGCTCC | TTGTCCCCTG | GACGGCAAGG | CCAGCAGCCT | 3960 |
| CGAAGGGATC | CCCCTAGAGA | AGGCTTGCGG | CCACCCCCT | ACAGACCGCG | CAGAGACGCT | 4020 |
| TTTGAAATTT | CTACTGAAGG | GCATTCTGGC | CCTAGCAATA | GGGACCGCTC | AGGGCCCGT | 4080 |
| GGGGCCCGTT | CTCACAACCC | TCGGAACCCA | ACGTCCACCG | CCATGGGCAG | CTCTGTGCCC | 4140 |
| AGCTACTGCC | AGCCCATCAC | CACTGTGACG | GCTTCTGCTT | CGGTGACTGT | TGCTGTGCAT | 4200 |

```
CCCCCGCCTG GACCTGGGCG CAACCCCCGA GGGGGGCCCT GTCCAGGCTA TGAGAGCTAC      4260

CCTGAGACTG ATCACGGGGT ATTTGAGGAT CCTCATGTGC CTTTTCATGT CAGGTGTGAG      4320

AGGAGGGACT CAAAGGTGGA GGTCATAGAG CTACAGGACG TGGAATGTGA GGAGAGGCCG      4380

TGGGGGAGCA GCTCCAACTG AGGGTAATTA AAATCTGAAG CAAAGAGGCC AAAGATTGGA      4440

AAGCCCCGCC CCCACCTCTT TCCAGAACTG CTTGAAGAGA ACTGCTTGGA ATTATGGAA       4500

GGCAGTTCAT TGTTACTGTA ACTGATTGTA TTATTKKGTG AAATATTTCT ATAAATATTT      4560

AARAGGTGTA CACATGTAAT ATACATGGAA ATGCTGTACA GTCTATTTCC TGGGGCCTCT      4620

CCACTCCTGC CCCAGAGTGG GGAGACCACA GGGGCCCTTT CCCCTGTGTA CATTGGTCTC      4680

TGTGCCACAA CCAAGCTTAA CTTAGTTTTA AAAAAAATCT CCCAGCATAT GTCGCTGCTG      4740

CTTAAATATT GTATAATTTA CTTGTATAAT TCTATGCAAA TATTGCTTAT GTAATAGGAT      4800

TATTTGTAAA GGTTTCTGTT TAAAATATTT TAAATTTGCA TATCACAACC CTGTGGTAGG      4860

ATGAATTGTT ACTGTTAACT TTTGAACACG CTATGCGTGG TAATTGTTTA ACGAGCAGAC      4920

ATGAAGAAAA CAGGTTAATC CCAGTGGCTT CTCTAGGGGT AGTTGTATAT GGTTCGCATG      4980

GGTGGATGTG TGTGTGCATG TGACTTTCCA ATGTACTGTA TTGTGGTTTG TTGTTGTTGT      5040

TGCTGTTGTT GTTCATTTTG GTGTTTTGG TTGCTTTGTA TGATCTTAGC TCTGGCCTAG       5100

GTGGGCTGGG AAGGTCCAGG TCTTTTTCTG TCGTGATGCT GGTGGAAAGG TGACCCCAAT      5160

CATCTGTCCT ATTCTCTGGG ACTATTC                                          5187
```

( 2 ) INFORMATION FOR SEQ ID NO:4:

( i ) SEQUENCE CHARACTERISTICS:
        ( A ) LENGTH: 1311 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met Val Ala Pro Asp Ser Glu Ala Pro Ser Asn Pro Arg Ile Thr Ala
  1               5                  10                  15

Ala His Glu Ser Pro Cys Ala Thr Glu Ala Arg His Ser Ala Asp Leu
             20                  25                  30

Tyr Ile Arg Thr Ser Trp Val Asp Ala Ala Leu Ala Leu Ser Glu Leu
         35                  40                  45

Glu Lys Gly Asn Ile Glu Gly Gly Arg Thr Ser Leu Trp Ile Arg Ala
     50                  55                  60

Trp Leu Gln Glu Gln Leu Phe Ile Leu Gly Cys Phe Leu Gln Gly Asp
 65                  70                  75                  80

Ala Gly Lys Val Leu Phe Val Ala Ile Leu Val Leu Ser Thr Phe Cys
                 85                  90                  95

Val Gly Leu Lys Ser Ala Gln Ile His Thr Arg Val Asp Gln Leu Trp
            100                 105                 110

Val Gln Glu Gly Gly Arg Leu Glu Ala Glu Leu Lys Tyr Thr Ala Gln
        115                 120                 125

Ala Leu Gly Glu Ala Asp Ser Ser Thr His Gln Leu Val Ile Gln Thr
    130                 135                 140

Ala Lys Asp Pro Asp Val Ser Leu Leu His Pro Gly Ala Leu Leu Glu
145                 150                 155                 160

His Leu Lys Val Val His Ala Ala Thr Arg Val Thr Val His Met Tyr
                165                 170                 175
```

```
Asp  Ile  Glu  Trp  Arg  Leu  Lys  Asp  Leu  Cys  Tyr  Ser  Pro  Ser  Ile  Pro
               180                 185                      190
Asp  Phe  Glu  Gly  Tyr  His  His  Ile  Glu  Ser  Ile  Ile  Asp  Asn  Val  Ile
          195                 200                      205
Pro  Cys  Ala  Ile  Ile  Thr  Pro  Leu  Asp  Cys  Phe  Trp  Glu  Gly  Ser  Lys
     210                 215                      220
Leu  Leu  Gly  Pro  Asp  Tyr  Pro  Ile  Tyr  Val  Pro  His  Leu  Lys  His  Lys
225                      230                      235                      240
Leu  Gln  Trp  Thr  His  Leu  Asn  Pro  Leu  Glu  Val  Val  Glu  Glu  Val  Lys
                    245                      250                      255
Lys  Leu  Lys  Phe  Gln  Phe  Pro  Leu  Ser  Thr  Ile  Glu  Ala  Tyr  Met  Lys
               260                 265                      270
Arg  Ala  Gly  Ile  Thr  Ser  Ala  Tyr  Met  Lys  Lys  Pro  Cys  Leu  Asp  Pro
          275                 280                      285
Thr  Asp  Pro  His  Cys  Pro  Ala  Thr  Ala  Pro  Asn  Lys  Lys  Ser  Gly  His
     290                 295                      300
Ile  Pro  Asp  Val  Ala  Ala  Glu  Leu  Ser  His  Gly  Cys  Tyr  Gly  Phe  Ala
305                      310                      315                      320
Ala  Ala  Tyr  Met  His  Trp  Pro  Glu  Gln  Leu  Ile  Val  Gly  Gly  Ala  Thr
                    325                      330                      335
Arg  Asn  Ser  Thr  Ser  Ala  Leu  Arg  Lys  Ala  Arg  Xaa  Leu  Gln  Thr  Val
               340                      345                 350
Val  Gln  Leu  Met  Gly  Glu  Arg  Glu  Met  Tyr  Glu  Tyr  Trp  Ala  Asp  His
          355                      360                      365
Tyr  Lys  Val  His  Gln  Ile  Gly  Trp  Asn  Gln  Glu  Lys  Ala  Ala  Ala  Val
     370                      375                      380
Leu  Asp  Ala  Trp  Gln  Arg  Lys  Phe  Ala  Ala  Glu  Val  Arg  Lys  Ile  Thr
385                      390                      395                      400
Thr  Ser  Gly  Ser  Val  Ser  Ser  Ala  Tyr  Ser  Phe  Tyr  Pro  Phe  Ser  Thr
                    405                      410                      415
Ser  Thr  Leu  Asn  Asp  Ile  Leu  Gly  Lys  Phe  Ser  Glu  Val  Ser  Leu  Lys
               420                      425                      430
Asn  Ile  Ile  Leu  Gly  Tyr  Met  Phe  Met  Leu  Ile  Tyr  Val  Ala  Val  Thr
          435                      440                      445
Leu  Ile  Gln  Trp  Arg  Asp  Pro  Ile  Arg  Ser  Gln  Ala  Gly  Val  Gly  Ile
     450                      455                      460
Ala  Gly  Val  Leu  Leu  Leu  Ser  Ile  Thr  Val  Ala  Ala  Gly  Leu  Gly  Phe
465                      470                      475                      480
Cys  Ala  Leu  Leu  Gly  Ile  Pro  Phe  Asn  Ala  Ser  Ser  Thr  Gln  Ile  Val
                    485                      490                      495
Pro  Phe  Leu  Ala  Leu  Gly  Leu  Gly  Val  Gln  Asp  Met  Phe  Leu  Leu  Thr
               500                      505                      510
His  Thr  Tyr  Val  Glu  Gln  Ala  Gly  Asp  Val  Pro  Arg  Glu  Glu  Arg  Thr
          515                      520                      525
Gly  Leu  Val  Leu  Lys  Lys  Ser  Gly  Leu  Ser  Val  Leu  Leu  Ala  Ser  Leu
     530                      535                      540
Cys  Asn  Val  Met  Ala  Phe  Leu  Ala  Ala  Ala  Leu  Leu  Pro  Ile  Pro  Ala
545                      550                      555                      560
Phe  Arg  Val  Phe  Cys  Leu  Gln  Ala  Ala  Ile  Leu  Leu  Leu  Phe  Asn  Leu
                    565                      570                      575
Gly  Ser  Ile  Leu  Leu  Val  Phe  Pro  Ala  Met  Ile  Ser  Leu  Asp  Leu  Arg
               580                      585                      590
Arg  Arg  Ser  Ala  Ala  Arg  Ala  Asp  Leu  Leu  Cys  Cys  Leu  Met  Pro  Glu
          595                      600                      605
```

```
Ser  Pro  Leu  Pro  Lys  Lys  Lys  Ile  Pro  Glu  Arg  Ala  Lys  Thr  Arg  Lys
     610            615                      620

Asn  Asp  Lys  Thr  His  Arg  Ile  Asp  Thr  Thr  Arg  Gln  Pro  Leu  Asp  Pro
625                      630                      635                           640

Asp  Val  Ser  Glu  Asn  Val  Thr  Lys  Thr  Cys  Leu  Ser  Val  Ser  Leu
                    645                      650                      655

Thr  Lys  Trp  Ala  Lys  Asn  Gln  Tyr  Ala  Pro  Phe  Ile  Met  Arg  Pro  Ala
               660                      665                      670

Val  Lys  Val  Thr  Ser  Met  Leu  Ala  Leu  Ile  Ala  Val  Ile  Leu  Thr  Ser
          675                      680                      685

Val  Trp  Gly  Ala  Thr  Lys  Val  Lys  Asp  Gly  Leu  Asp  Leu  Thr  Asp  Ile
     690                      695                      700

Val  Pro  Glu  Asn  Thr  Asp  Glu  His  Glu  Phe  Leu  Ser  Arg  Gln  Glu  Lys
705                      710                      715                           720

Tyr  Phe  Gly  Phe  Tyr  Asn  Met  Tyr  Ala  Val  Thr  Gln  Gly  Asn  Phe  Glu
                    725                      730                      735

Tyr  Pro  Thr  Asn  Gln  Lys  Leu  Leu  Tyr  Glu  Tyr  His  Asp  Gln  Phe  Val
               740                      745                      750

Arg  Ile  Pro  Asn  Ile  Ile  Lys  Asn  Asp  Asn  Gly  Gly  Leu  Thr  Lys  Phe
               755                      760                      765

Trp  Leu  Ser  Leu  Phe  Arg  Asp  Trp  Leu  Leu  Asp  Leu  Gln  Val  Ala  Phe
     770                      775                      780

Asp  Lys  Glu  Val  Ala  Ser  Gly  Cys  Ile  Thr  Gln  Glu  Tyr  Trp  Cys  Lys
785                      790                      795                           800

Asn  Ala  Ser  Asp  Glu  Gly  Ile  Leu  Ala  Tyr  Lys  Leu  Met  Val  Gln  Thr
                    805                      810                      815

Gly  His  Val  Asp  Asn  Pro  Ile  Asp  Lys  Ser  Leu  Ile  Thr  Ala  Gly  His
               820                      825                      830

Arg  Leu  Val  Asp  Lys  Asp  Gly  Ile  Ile  Asn  Pro  Lys  Ala  Phe  Tyr  Asn
          835                      840                      845

Tyr  Leu  Ser  Ala  Trp  Ala  Thr  Asn  Asp  Ala  Leu  Ala  Tyr  Gly  Ala  Ser
     850                      855                      860

Gln  Gly  Asn  Leu  Lys  Pro  Gln  Pro  Gln  Arg  Trp  Ile  His  Ser  Pro  Glu
865                      870                      875                           880

Asp  Val  His  Leu  Glu  Ile  Lys  Lys  Ser  Ser  Pro  Leu  Ile  Tyr  Thr  Gln
                    885                      890                      895

Leu  Pro  Phe  Tyr  Leu  Ser  Gly  Leu  Ser  Asp  Thr  Xaa  Ser  Ile  Lys  Thr
               900                      905                      910

Leu  Ile  Arg  Ser  Val  Arg  Asp  Leu  Cys  Leu  Lys  Tyr  Glu  Ala  Lys  Gly
          915                      920                      925

Leu  Pro  Asn  Phe  Pro  Ser  Gly  Ile  Pro  Phe  Leu  Phe  Trp  Glu  Gln  Tyr
     930                      935                      940

Leu  Tyr  Leu  Arg  Thr  Ser  Leu  Leu  Leu  Ala  Leu  Ala  Cys  Ala  Leu  Ala
945                      950                      955                           960

Ala  Val  Phe  Ile  Ala  Val  Met  Val  Leu  Leu  Leu  Asn  Ala  Trp  Ala  Ala
                    965                      970                      975

Val  Leu  Val  Thr  Leu  Ala  Leu  Ala  Thr  Leu  Val  Leu  Gln  Leu  Leu  Gly
               980                      985                      990

Val  Met  Ala  Leu  Leu  Gly  Val  Lys  Leu  Ser  Ala  Met  Pro  Ala  Val  Leu
          995                      1000                     1005

Leu  Val  Leu  Ala  Ile  Gly  Arg  Gly  Val  His  Phe  Thr  Val  His  Leu  Cys
     1010                     1015                     1020

Leu  Gly  Phe  Val  Thr  Ser  Ile  Gly  Cys  Lys  Arg  Arg  Arg  Ala  Ser  Leu
```

|      |      |      |      |      |      |      |      |      |      |      |      |      |      |
|---|---|---|---|---|---|---|---|---|---|---|---|---|---|
| 1025 | | | | 1030 | | | | 1035 | | | | 1040 | |
| Ala | Leu | Glu | Ser | Val | Leu | Ala | Pro | Val | Val | His | Gly | Ala | Leu | Ala | Ala |
| | | | | 1045 | | | | 1050 | | | | 1055 | |
| Ala | Leu | Ala | Ala | Ser | Met | Leu | Ala | Ala | Ser | Glu | Cys | Gly | Phe | Val | Ala |
| | | | | 1060 | | | | 1065 | | | | 1070 | |
| Arg | Leu | Phe | Leu | Arg | Leu | Leu | Leu | Asp | Ile | Val | Phe | Leu | Gly | Leu | Ile |
| | | | | 1075 | | | | 1080 | | | | 1085 | |
| Asp | Gly | Leu | Leu | Phe | Phe | Pro | Ile | Val | Leu | Ser | Ile | Leu | Gly | Pro | Ala |
| | | | | 1090 | | | | 1095 | | | | 1100 | |
| Ala | Glu | Val | Arg | Pro | Ile | Glu | His | Pro | Glu | Arg | Leu | Ser | Thr | Pro | Ser |
| 1105 | | | | 1110 | | | | 1115 | | | | 1120 | |
| Pro | Lys | Cys | Ser | Pro | Ile | His | Pro | Arg | Lys | Ser | Ser | Ser | Ser | Gly |
| | | | | 1125 | | | | 1130 | | | | 1135 | |
| Gly | Gly | Asp | Lys | Ser | Ser | Arg | Thr | Ser | Lys | Ser | Ala | Pro | Arg | Pro | Cys |
| | | | | 1140 | | | | 1145 | | | | 1150 | |
| Ala | Pro | Ser | Leu | Thr | Thr | Ile | Thr | Glu | Glu | Pro | Ser | Ser | Trp | His | Ser |
| | | | | 1155 | | | | 1160 | | | | 1165 | |
| Ser | Ala | His | Ser | Val | Gln | Ser | Ser | Met | Gln | Ser | Ile | Val | Val | Gln | Pro |
| | | | | 1170 | | | | 1175 | | | | 1180 | |
| Glu | Val | Val | Val | Glu | Thr | Thr | Thr | Tyr | Asn | Gly | Ser | Asp | Ser | Ala | Ser |
| 1185 | | | | 1190 | | | | 1195 | | | | 1200 | |
| Gly | Arg | Ser | Thr | Pro | Thr | Lys | Ser | Ser | His | Gly | Gly | Ala | Ile | Thr | Thr |
| | | | | 1205 | | | | 1210 | | | | 1215 | |
| Thr | Lys | Val | Thr | Ala | Thr | Ala | Asn | Ile | Lys | Val | Glu | Val | Val | Thr | Pro |
| | | | | 1220 | | | | 1225 | | | | 1230 | |
| Ser | Asp | Arg | Lys | Ser | Arg | Arg | Ser | Tyr | His | Tyr | Tyr | Asp | Arg | Arg | Arg |
| | | | | 1235 | | | | 1240 | | | | 1245 | |
| Asp | Arg | Asp | Glu | Asp | Arg | Asp | Arg | Asp | Arg | Glu | Arg | Asp | Arg | Asp | Arg |
| | | | | 1250 | | | | 1255 | | | | 1260 | |
| Asp | Arg | Asp | Arg | Asp | Arg | Asp | Arg | Asp | Arg | Asp | Arg | Asp | Arg | Asp | Arg |
| 1265 | | | | 1270 | | | | 1275 | | | | 1280 | |
| Glu | Arg | Ser | Arg | Glu | Arg | Asp | Arg | Arg | Asp | Arg | Tyr | Arg | Asp | Glu | Arg |
| | | | | 1285 | | | | 1290 | | | | 1295 | |
| Asp | His | Arg | Ala | Ser | Pro | Arg | Glu | Lys | Arg | Gln | Arg | Phe | Trp | Thr |
| | | | | 1300 | | | | 1305 | | | | 1310 | |

( 2 ) INFORMATION FOR SEQ ID NO:5:

( i ) SEQUENCE CHARACTERISTICS:
        ( A ) LENGTH: 4434 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

| | | | | | |
|---|---|---|---|---|---|
| CGAAACAAGA | GAGCGAGTGA | GAGTAGGGAG | AGCGTCTGTG | TTGTGTGTTG | AGTGTCGCCC | 60 |
| ACGCACACAG | GCGCAAAACA | GTGCACACAG | ACGCCCGCTG | GGCAAGAGAG | AGTGAGAGAG | 120 |
| AGAAACAGCG | GCGCGCGCTC | GCCTAATGAA | GTTGTTGGCC | TGGCTGGCGT | GCCGCATCCA | 180 |
| CGAGATACAG | ATACATCTCT | CATGGACCGC | GACAGCCTCC | CACGCGTTCC | GGACACACAC | 240 |
| GGCGATGTGG | TCGATGAGAA | ATTATTCTCG | GATCTTTACA | TACGCACCAG | CTGGGTGGAC | 300 |
| GCCCAAGTGG | CGCTCGATCA | GATAGATAAG | GGCAAAGCGC | GTGGCAGCCG | CACGGCGATC | 360 |
| TATCTGCGAT | CAGTATTCCA | GTCCCACCTC | GAAACCCTCG | GCAGCTCCGT | GCAAAAGCAC | 420 |

| | | | | | | |
|---|---|---|---|---|---|---|
| GCGGGCAAGG | TGCTATTCGT | GGCTATCCTG | GTGCTGAGCA | CCTTCTGCGT | CGGCCTGAAG | 480 |
| AGCGCCCAGA | TCCACTCCAA | GGTGCACCAG | CTGTGGATCC | AGGAGGGCGG | CCGGCTGGAG | 540 |
| GCGGAACTGG | CCTACACACA | GAAGACGATC | GGCGAGGACG | AGTCGGCCAC | GCATCAGCTG | 600 |
| CTCATTCAGA | CGACCCACGA | CCCGAACGCC | TCCGTCCTGC | ATCCGCAGGC | GCTGCTTGCC | 660 |
| CACCTGGAGG | TCCTGGTCAA | GGCCACCGCC | GTCAAGGTGC | ACCTCTACGA | CACCGAATGG | 720 |
| GGGCTGCGCG | ACATGTGCAA | CATGCCGAGC | ACGCCCTCCT | TCGAGGGCAT | CTACTACATC | 780 |
| GAGCAGATCC | TGCGCCACCT | CATTCCGTGC | TCGATCATCA | CGCCGCTGGA | CTGTTTCTGG | 840 |
| GAGGGAAGCC | AGCTGTTGGG | TCCGGAATCA | GCGGTCGTTA | TACCAGGCCT | CAACCAACGA | 900 |
| CTCCTGTGGA | CCACCCTGAA | TCCCGCCTCT | GTGATGCAGT | ATATGAAACA | AAAGATGTCC | 960 |
| GAGGAAAAGA | TCAGCTTCGA | CTTCGAGACC | GTGGAGCAGT | ACATGAAGCG | TGCGGCCATT | 1020 |
| GGCAGTGGCT | ACATGGAGAA | GCCCTGCCTG | AACCCACTGA | ATCCAATTG | CCCGGACACG | 1080 |
| GCACCGAACA | AGAACAGCAC | CCAGCCGCCG | GATGTGGGAG | CCATCCTGTC | CGGAGGCTGC | 1140 |
| TACGGTTATG | CCGCGAAGCA | CATGCACTGG | CCGGAGGAGC | TGATTGTGGG | CGGACGGAAG | 1200 |
| AGGAACCGCA | GCGGACACTT | GAGGAAGGCC | CAGGCCCTGC | AGTCGGTGGT | GCAGCTGATG | 1260 |
| ACCGAGAAGG | AAATGTACGA | CCAGTGGCAG | GACAACTACA | AGGTGCACCA | TCTTGGATGG | 1320 |
| ACGCAGGAGA | AGGCAGCGGA | GGTTTTGAAC | GCCTGGCAGC | GCAACTTTTC | GCGGGAGGTG | 1380 |
| GAACAGCTGC | TACGTAAACA | GTCGAGAATT | GCCACCAACT | ACGATATCTA | CGTGTTCAGC | 1440 |
| TCGGCTGCAC | TGGATGACAT | CCTGGCCAAG | TTCTCCCATC | CCAGCGCCTT | GTCCATTGTC | 1500 |
| ATCGGCGTGG | CCGTCACCGT | TTTGTATGCC | TTTTGCACGC | TCCTCCGCTG | GAGGGACCCC | 1560 |
| GTCCGTGGCC | AGAGCAGTGT | GGGCGTGGCC | GGAGTTCTGC | TCATGTGCTT | CAGTACCGCC | 1620 |
| GCCGGATTGG | GATTGTCAGC | CCTGCTCGGT | ATCGTTTTCA | ATGCGCTGAC | CGCTGCCTAT | 1680 |
| GCGGAGAGCA | ATCGGCGGGA | GCAGACCAAG | CTGATTCTCA | AGAACGCCAG | CACCCAGGTG | 1740 |
| GTTCCGTTTT | TGGCCCTTGG | TCTGGGCGTC | GATCACATCT | TCATAGTGGG | ACCGAGCATC | 1800 |
| CTGTTCAGTG | CCTGCAGCAC | CGCAGGATCC | TTCTTTGCGG | CCGCCTTTAT | TCCGGTGCCG | 1860 |
| GCTTTGAAGG | TATTCTGTCT | GCAGGCTGCC | ATCGTAATGT | GCTCCAATTT | GGCAGCGGCT | 1920 |
| CTATTGGTTT | TTCCGGCCAT | GATTTCGTTG | GATCTACGGA | GACGTACCGC | CGGCAGGGCG | 1980 |
| GACATCTTCT | GCTGCTGTTT | TCCGGTGTGG | AAGGAACAGC | CGAAGGTGGC | ACCTCCGGTG | 2040 |
| CTGCCGCTGA | ACAACAACAA | CGGGCGCGGG | GCCCGGCATC | CGAAGAGCTG | CAACAACAAC | 2100 |
| AGGGTGCCGC | TGCCCGCCCA | GAATCCTCTG | CTGGAACAGA | GGGCAGACAT | CCCTGGGAGC | 2160 |
| AGTCACTCAC | TGGCGTCCTT | CTCCCTGGCA | ACCTTCGCCT | TTCAGCACTA | CACTCCCTTC | 2220 |
| CTCATGCGCA | GCTGGGTGAA | GTTCCTGACC | GTTATGGGTT | TCCTGGCGGC | CCTCATATCC | 2280 |
| AGCTTGTATG | CCTCCACGCG | CCTTCAGGAT | GGCCTGGACA | TTATTGATCT | GGTGCCCAAG | 2340 |
| GACAGCAACG | AGCACAAGTT | CCTGGATGCT | CAAACTCGGC | TCTTTGGCTT | CTACAGCATG | 2400 |
| TATGCGGTTA | CCCAGGGCAA | CTTTGAATAT | CCCACCCAGC | AGCAGTTGCT | CAGGGACTAC | 2460 |
| CATGATTCCT | TTGTGCGGGT | GCCACATGTG | ATCAAGAATG | ATAACGGTGG | ACTGCCGGAC | 2520 |
| TTCTGGCTGC | TGCTCTTCAG | CGAGTGGCTG | GGTAATCTGC | AAAAGATATT | CGACGAGGAA | 2580 |
| TACCGCGACG | GACGGCTGAC | CAAGGAGTGC | TGGTTCCCAA | ACGCCAGCAG | CGATGCCATC | 2640 |
| CTGGCCTACA | AGCTAATCGT | GCAAACCGGC | CATGTGGACA | ACCCCGTGGA | CAAGGAACTG | 2700 |
| GTGCTCACCA | ATCGCCTGGT | CAACAGCGAT | GGCATCATCA | ACCAACGCGC | CTTCTACAAC | 2760 |
| TATCTGTCGG | CATGGGCCAC | CAACGACGTC | TTCGCCTACG | GAGCTTCTCA | GGGCAAATTG | 2820 |

| | | | | | |
|---|---|---|---|---|---|
| TATCCGGAAC | CGCGCCAGTA | TTTTCACCAA | CCCAACGAGT | ACGATCTTAA | GATACCCAAG | 2880
| AGTCTGCCAT | TGGTCTACGC | TCAGATGCCC | TTTTACCTCC | ACGGACTAAC | AGATACCTCG | 2940
| CAGATCAAGA | CCCTGATAGG | TCATATTCGC | GACCTGAGCG | TCAAGTACGA | GGGCTTCGGC | 3000
| CTGCCCAACT | ATCCATCGGG | CATTCCCTTC | ATCTTCTGGG | AGCAGTACAT | GACCCTGCGC | 3060
| TCCTCACTGG | CCATGATCCT | GGCCTGCGTG | CTACTCGCCG | CCCTGGTGCT | GGTCTCCCTG | 3120
| CTCCTGCTCT | CCGTTTGGGC | CGCCGTTCTC | GTGATCCTCA | GCGTTCTGGC | CTCGCTGGCC | 3180
| CAGATCTTTG | GGGCCATGAC | TCTGCTGGGC | ATCAAACTCT | CGGCCATTCC | GGCAGTCATA | 3240
| CTCATCCTCA | GCGTGGGCAT | GATGCTGTGC | TTCAATGTGC | TGATATCACT | GGGCTTCATG | 3300
| ACATCCGTTG | GCAACCGACA | GCGCCGCGTC | CAGCTGAGCA | TGCAGATGTC | CCTGGGACCA | 3360
| CTTGTCCACG | GCATGCTGAC | CTCCGGAGTG | GCCGTGTTCA | TGCTCTCCAC | GTCGCCCTTT | 3420
| GAGTTTGTGA | TCCGGCACTT | CTGCTGGCTT | CTGCTGGTGG | TCTTATGCGT | GGCGCCTGC | 3480
| AACAGCCTTT | TGGTGTTCCC | CATCCTACTG | AGCATGGTGG | GACCGGAGGC | GGAGCTGGTG | 3540
| CCGCTGGAGC | ATCCAGACCG | CATATCCACG | CCCTCTCCGC | TGCCCGTGCG | CAGCAGCAAG | 3600
| AGATCGGGCA | AATCCTATGT | GGTGCAGGGA | TCGCGATCCT | CGCGAGGCAG | CTGCCAGAAG | 3660
| TCGCATCACC | ACCACCACAA | AGACCTTAAT | GATCCATCGC | TGACGACGAT | CACCGAGGAG | 3720
| CCGCAGTCGT | GGAAGTCCAG | CAACTCGTCC | ATCCAGATGC | CAATGATTG | GACCTACCAG | 3780
| CCGCGGGAAC | AGCGACCCGC | CTCCTACGCG | GCCCGCCCC | CCGCCTATCA | CAAGGCCGCC | 3840
| GCCCAGCAGC | ACCACCAGCA | TCAGGGCCCG | CCCACAACGC | CCCGCCTCC | CTTCCCGACG | 3900
| GCCTATCCGC | CGGAGCTGCA | GAGCATCGTG | GTGCAGCCGG | AGGTGACGGT | GGAGACGACG | 3960
| CACTCGGACA | GCAACACCAC | CAAGGTGACG | GCCACGGCCA | ACATCAAGGT | GGAGCTGGCC | 4020
| ATGCCCGGCA | GGGCGGTGCG | CAGCTATAAC | TTTACGAGTT | AGCACTAGCA | CTAGTTCCTG | 4080
| TAGCTATTAG | GACGTATCTT | TAGACTCTAG | CCTAAGCCGT | AACCCTATTT | GTATCTGTAA | 4140
| AATCGATTTG | TCCAGCGGGT | CTGCTGAGGA | TTTCGTTCTC | ATGGATTCTC | ATGGATTCTC | 4200
| ATGGATGCTT | AAATGGCATG | GTAATTGGCA | AAATATCAAT | TTTTGTGTCT | CAAAAAGATG | 4260
| CATTAGCTTA | TGGTTTCAAG | ATACATTTTT | AAAGAGTCCG | CCAGATATTT | ATATAAAAAA | 4320
| AATCCAAAAT | CGACGTATCC | ATGAAAATTG | AAAAGCTAAG | CAGACCCGTA | TGTATGTATA | 4380
| TGTGTATGCA | TGTTAGTTAA | TTTCCCGAAG | TCCGGTATTT | ATAGCAGCTG | CCTT | 4434

(2) INFORMATION FOR SEQ ID NO:6:

(i) SEQUENCE CHARACTERISTICS:
        (A) LENGTH: 1285 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met  Asp  Arg  Asp  Ser  Leu  Pro  Arg  Val  Pro  Asp  Thr  His  Gly  Asp  Val
  1                  5                   10                      15

Val  Asp  Glu  Lys  Leu  Phe  Ser  Asp  Leu  Tyr  Ile  Arg  Thr  Ser  Trp  Val
             20                      25                      30

Asp  Ala  Gln  Val  Ala  Leu  Asp  Gln  Ile  Asp  Lys  Gly  Lys  Ala  Arg  Gly
             35                      40                      45

Ser  Arg  Thr  Ala  Ile  Tyr  Leu  Arg  Ser  Val  Phe  Gln  Ser  His  Leu  Glu
        50                      55                      60

Thr  Leu  Gly  Ser  Ser  Val  Gln  Lys  His  Ala  Gly  Lys  Val  Leu  Phe  Val
```

-continued

|  | 65 |  |  |  |  | 70 |  |  |  | 75 |  |  |  | 80 |  |
|---|---|---|---|---|---|---|---|---|---|---|---|---|---|---|---|
| Ala | Ile | Leu | Val | Leu 85 | Ser | Thr | Phe | Cys | Val 90 | Gly | Leu | Lys | Ser | Ala 95 | Gln |
| Ile | His | Ser | Lys 100 | Val | His | Gln | Leu 105 | Trp | Ile | Gln | Glu | Gly 110 | Gly | Arg | Leu |
| Glu | Ala | Glu | Leu 115 | Ala | Tyr | Thr | Gln 120 | Lys | Thr | Ile | Gly | Glu 125 | Asp | Glu | Ser |
| Ala | Thr 130 | His | Gln | Leu | Leu | Ile 135 | Gln | Thr | Thr | His | Asp 140 | Pro | Asn | Ala | Ser |
| Val 145 | Leu | His | Pro | Gln | Ala 150 | Leu | Leu | Ala | His | Leu 155 | Glu | Val | Leu | Val | Lys 160 |
| Ala | Thr | Ala | Val | Lys 165 | Val | His | Leu | Tyr | Asp 170 | Thr | Glu | Trp | Gly | Leu 175 | Arg |
| Asp | Met | Cys | Asn 180 | Met | Pro | Ser | Thr | Pro 185 | Ser | Phe | Glu | Gly | Ile 190 | Tyr | Tyr |
| Ile | Glu | Gln 195 | Ile | Leu | Arg | His | Leu 200 | Ile | Pro | Cys | Ser | Ile 205 | Ile | Thr | Pro |
| Leu | Asp 210 | Cys | Phe | Trp | Glu | Gly 215 | Ser | Gln | Leu | Leu | Gly 220 | Pro | Glu | Ser | Ala |
| Val 225 | Val | Ile | Pro | Gly | Leu 230 | Asn | Gln | Arg | Leu | Leu 235 | Trp | Thr | Thr | Leu | Asn 240 |
| Pro | Ala | Ser | Val | Met 245 | Gln | Tyr | Met | Lys | Gln 250 | Lys | Met | Ser | Glu | Glu 255 | Lys |
| Ile | Ser | Phe | Asp 260 | Phe | Glu | Thr | Val | Glu 265 | Gln | Tyr | Met | Lys | Arg 270 | Ala | Ala |
| Ile | Gly | Ser 275 | Gly | Tyr | Met | Glu | Lys 280 | Pro | Cys | Leu | Asn | Pro 285 | Leu | Asn | Pro |
| Asn | Cys 290 | Pro | Asp | Thr | Ala | Pro 295 | Asn | Lys | Asn | Ser | Thr 300 | Gln | Pro | Pro | Asp |
| Val 305 | Gly | Ala | Ile | Leu | Ser 310 | Gly | Gly | Cys | Tyr | Gly 315 | Tyr | Ala | Ala | Lys | His 320 |
| Met | His | Trp | Pro | Glu 325 | Glu | Leu | Ile | Val | Gly 330 | Gly | Arg | Lys | Arg | Asn 335 | Arg |
| Ser | Gly | His | Leu 340 | Arg | Lys | Ala | Gln | Ala 345 | Leu | Gln | Ser | Val | Val 350 | Gln | Leu |
| Met | Thr | Glu 355 | Lys | Glu | Met | Tyr | Asp 360 | Gln | Trp | Gln | Asp | Asn 365 | Tyr | Lys | Val |
| His | His 370 | Leu | Gly | Trp | Thr | Gln 375 | Glu | Lys | Ala | Ala | Glu 380 | Val | Leu | Asn | Ala |
| Trp 385 | Gln | Arg | Asn | Phe | Ser 390 | Arg | Glu | Val | Glu | Gln 395 | Leu | Leu | Arg | Lys | Gln 400 |
| Ser | Arg | Ile | Ala | Thr 405 | Asn | Tyr | Asp | Ile | Tyr 410 | Val | Phe | Ser | Ser | Ala 415 | Ala |
| Leu | Asp | Asp | Ile 420 | Leu | Ala | Lys | Phe | His 425 | Pro | Ser | Ala | Leu | Ser 430 | Ile |
| Val | Ile | Gly 435 | Val | Ala | Val | Thr | Val 440 | Leu | Tyr | Ala | Phe | Cys 445 | Thr | Leu | Leu |
| Arg | Trp 450 | Arg | Asp | Pro | Val | Arg 455 | Gly | Gln | Ser | Ser | Val 460 | Gly | Val | Ala | Gly |
| Val 465 | Leu | Leu | Met | Cys | Phe 470 | Ser | Thr | Ala | Ala | Gly 475 | Leu | Gly | Leu | Ser | Ala 480 |
| Leu | Leu | Gly | Ile | Val 485 | Phe | Asn | Ala | Leu | Thr 490 | Ala | Ala | Tyr | Ala | Glu 495 | Ser |

-continued

```
Asn Arg Arg Glu Gln Thr Lys Leu Ile Leu Lys Asn Ala Ser Thr Gln
            500                 505                 510

Val Val Pro Phe Leu Ala Leu Gly Leu Gly Val Asp His Ile Phe Ile
        515                 520                 525

Val Gly Pro Ser Ile Leu Phe Ser Ala Cys Ser Thr Ala Gly Ser Phe
    530                 535                 540

Phe Ala Ala Ala Phe Ile Pro Val Pro Ala Leu Lys Val Phe Cys Leu
545                 550                 555                 560

Gln Ala Ala Ile Val Met Cys Ser Asn Leu Ala Ala Leu Leu Val
                565                 570                 575

Phe Pro Ala Met Ile Ser Leu Asp Leu Arg Arg Arg Thr Ala Gly Arg
            580                 585                 590

Ala Asp Ile Phe Cys Cys Cys Phe Pro Val Trp Lys Glu Gln Pro Lys
        595                 600                 605

Val Ala Pro Pro Val Leu Pro Leu Asn Asn Asn Gly Arg Gly Ala
    610                 615                 620

Arg His Pro Lys Ser Cys Asn Asn Asn Arg Val Pro Leu Pro Ala Gln
625                 630                 635                 640

Asn Pro Leu Leu Glu Gln Arg Ala Asp Ile Pro Gly Ser Ser His Ser
                645                 650                 655

Leu Ala Ser Phe Ser Leu Ala Thr Phe Ala Phe Gln His Tyr Thr Pro
            660                 665                 670

Phe Leu Met Arg Ser Trp Val Lys Phe Leu Thr Val Met Gly Phe Leu
        675                 680                 685

Ala Ala Leu Ile Ser Ser Leu Tyr Ala Ser Thr Arg Leu Gln Asp Gly
    690                 695                 700

Leu Asp Ile Ile Asp Leu Val Pro Lys Asp Ser Asn Glu His Lys Phe
705                 710                 715                 720

Leu Asp Ala Gln Thr Arg Leu Phe Gly Phe Tyr Ser Met Tyr Ala Val
                725                 730                 735

Thr Gln Gly Asn Phe Glu Tyr Pro Thr Gln Gln Leu Leu Arg Asp
            740                 745                 750

Tyr His Asp Ser Phe Arg Val Pro His Val Ile Lys Asn Asp Asn Gly
        755                 760                 765

Gly Leu Pro Asp Phe Trp Leu Leu Phe Ser Glu Trp Leu Gly Asn
    770                 775                 780

Leu Gln Lys Ile Phe Asp Glu Glu Tyr Arg Asp Gly Arg Leu Thr Lys
785                 790                 795                 800

Glu Cys Trp Phe Pro Asn Ala Ser Ser Asp Ala Ile Leu Ala Tyr Lys
                805                 810                 815

Leu Ile Val Gln Thr Gly His Val Asp Asn Pro Val Asp Lys Glu Leu
            820                 825                 830

Val Leu Thr Asn Arg Leu Val Asn Ser Asp Gly Ile Ile Asn Gln Arg
        835                 840                 845

Ala Phe Tyr Asn Tyr Leu Ser Ala Trp Ala Thr Asn Asp Val Phe Ala
    850                 855                 860

Tyr Gly Ala Ser Gln Gly Lys Leu Tyr Pro Glu Pro Arg Gln Tyr Phe
865                 870                 875                 880

His Gln Pro Asn Glu Tyr Asp Leu Lys Ile Pro Lys Ser Leu Pro Leu
                885                 890                 895

Val Tyr Ala Gln Met Pro Phe Tyr Leu His Gly Leu Thr Asp Thr Ser
            900                 905                 910

Gln Ile Lys Thr Leu Ile Gly His Ile Arg Asp Leu Ser Val Lys Tyr
        915                 920                 925
```

```
Glu  Gly  Phe  Gly  Leu  Pro  Asn  Tyr  Pro  Ser  Gly  Ile  Pro  Phe  Ile  Phe
930                      935                940

Trp  Glu  Gln  Tyr  Met  Thr  Leu  Arg  Ser  Ser  Leu  Ala  Met  Ile  Leu  Ala
945                 950                 955                           960

Cys  Val  Leu  Leu  Ala  Ala  Leu  Val  Leu  Val  Ser  Leu  Leu  Leu  Leu  Ser
               965                 970                      975

Val  Trp  Ala  Ala  Val  Leu  Val  Ile  Leu  Ser  Val  Leu  Ala  Ser  Leu  Ala
          980                      985                           990

Gln  Ile  Phe  Gly  Ala  Met  Thr  Leu  Leu  Gly  Ile  Lys  Leu  Ser  Ala  Ile
          995                 1000                1005

Pro  Ala  Val  Ile  Leu  Ile  Leu  Ser  Val  Gly  Met  Met  Leu  Cys  Phe  Asn
          1010                1015                1020

Val  Leu  Ile  Ser  Leu  Gly  Phe  Met  Thr  Ser  Val  Gly  Asn  Arg  Gln  Arg
1025                1030                1035                          1040

Arg  Val  Gln  Leu  Ser  Met  Gln  Met  Ser  Leu  Gly  Pro  Leu  Val  His  Gly
               1045                1050                1055

Met  Leu  Thr  Ser  Gly  Val  Ala  Val  Phe  Met  Leu  Ser  Thr  Ser  Pro  Phe
               1060                1065                1070

Glu  Phe  Val  Ile  Arg  His  Phe  Cys  Trp  Leu  Leu  Leu  Val  Val  Leu  Cys
          1075                1080                1085

Val  Gly  Ala  Cys  Asn  Ser  Leu  Leu  Val  Phe  Pro  Ile  Leu  Leu  Ser  Met
     1090                1095                1100

Val  Gly  Pro  Glu  Ala  Glu  Leu  Val  Pro  Leu  Glu  His  Pro  Asp  Arg  Ile
1105                1110                1115                          1120

Ser  Thr  Pro  Ser  Pro  Leu  Pro  Val  Arg  Ser  Ser  Lys  Arg  Ser  Gly  Lys
               1125                1130                          1135

Ser  Tyr  Val  Val  Gln  Gly  Ser  Arg  Ser  Ser  Arg  Gly  Ser  Cys  Gln  Lys
               1140                1145                          1150

Ser  His  His  His  His  His  Lys  Asp  Leu  Asn  Asp  Pro  Ser  Leu  Thr  Thr
               1155                1160                     1165

Ile  Thr  Glu  Glu  Pro  Gln  Ser  Trp  Lys  Ser  Ser  Asn  Ser  Ser  Ile  Gln
     1170                     1175                1180

Met  Pro  Asn  Asp  Trp  Thr  Tyr  Gln  Pro  Arg  Glu  Gln  Arg  Pro  Ala  Ser
1185                1190                1195                          1200

Tyr  Ala  Ala  Pro  Pro  Pro  Ala  Tyr  His  Lys  Ala  Ala  Ala  Gln  Gln  His
                    1205                1210                          1215

His  Gln  His  Gln  Gly  Pro  Pro  Thr  Thr  Pro  Pro  Pro  Pro  Phe  Pro  Thr
               1220                     1225                     1230

Ala  Tyr  Pro  Pro  Glu  Leu  Gln  Ser  Ile  Val  Val  Gln  Pro  Glu  Val  Thr
          1235                1240                     1245

Val  Glu  Thr  Thr  His  Ser  Asp  Ser  Asn  Thr  Thr  Lys  Val  Thr  Ala  Thr
1250                     1255                     1260

Ala  Asn  Ile  Lys  Val  Glu  Leu  Ala  Met  Pro  Gly  Arg  Ala  Val  Arg  Ser
1265                     1270                1275                          1280

Tyr  Asn  Phe  Thr  Ser
               1285
```

( 2 ) INFORMATION FOR SEQ ID NO:7:

( i ) SEQUENCE CHARACTERISTICS:
     ( A ) LENGTH: 345 base pairs
     ( B ) TYPE: nucleic acid
     ( C ) STRANDEDNESS: single
     ( D ) TOPOLOGY: linear ( i i ) MOLECULE TYPE: DNA (genomic)

( x i ) SEQUENCE DESCRIPTION: SEQ ID NO:7:

| | | | | | |
|---|---|---|---|---|---|
| AAGGTCCATC | AGCTTTGGAT | ACAGGAAGGT | GGTTCGCTCG | AGCATGAGCT | AGCCTACACG | 60 |
| CAGAAATCGC | TCGGCGAGAT | GGACTCCTCC | ACGCACCAGC | TGCTAATCCA | AACNCCCAAA | 120 |
| GATATGGACG | CCTCGATACT | GCACCCGAAC | GCGCTACTGA | CGCACCTGGA | CGTGGTGAAG | 180 |
| AAAGCGATCT | CGGTGACGGT | GCACATGTAC | GACATACGT | GGAGNCTCAA | GGACATGTGC | 240 |
| TACTCGCCCA | GCATACCGAG | NTTCGATACG | CACTTTATCG | AGCAGATCTT | CGAGAACATC | 300 |
| ATACCGTGCG | CGATCATCAC | GCCGCTGGAT | TGCTTTTGGG | AGGA | | 345 |

( 2 ) INFORMATION FOR SEQ ID NO:8:

( i ) SEQUENCE CHARACTERISTICS:
( A ) LENGTH: 115 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

Lys Val His Gln Leu Trp Ile Gln Glu Gly Gly Ser Leu Glu His Glu
1               5                   10                  15

Leu Ala Tyr Thr Gln Lys Ser Leu Gly Glu Met Asp Ser Ser Thr His
            20                  25                  30

Gln Leu Leu Ile Gln Thr Pro Lys Asp Met Asp Ala Ser Ile Leu His
        35                  40                  45

Pro Asn Ala Leu Leu Thr His Leu Asp Val Val Lys Lys Ala Ile Ser
    50                  55                  60

Val Thr Val His Met Tyr Asp Ile Thr Trp Xaa Leu Lys Asp Met Cys
65                  70                  75                  80

Tyr Ser Pro Ser Ile Pro Xaa Phe Asp Thr His Phe Ile Glu Gln Ile
                85                  90                  95

Phe Glu Asn Ile Ile Pro Cys Ala Ile Ile Thr Pro Leu Asp Cys Phe
            100                 105                 110

Trp Glu Gly
        115

( 2 ) INFORMATION FOR SEQ ID NO:9:

( i ) SEQUENCE CHARACTERISTICS:
( A ) LENGTH: 5187 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:9:

| | | | | | |
|---|---|---|---|---|---|
| GGGTCTGTCA | CCCGGAGCCG | GAGTCCCCGG | CGGCCAGCAG | CGTCCTCGCG | AGCCGAGCGC | 60 |
| CCAGGCGCGC | CCGGAGCCCG | CGGCGGCGG | GGCAACATGG | CCTCGGCTGG | TAACGCCGCC | 120 |
| GGGGCCCTGG | GCAGGCAGGC | CGGCGGCGGG | AGGCGCAGAC | GGACCGGGGG | ACCGCACCGC | 180 |
| GCCGCGCCGG | ACCGGGACTA | TCTGCACCGG | CCCAGCTACT | GCGACGCCGC | CTTCGCTCTG | 240 |
| GAGCAGATTT | CCAAGGGGAA | GGCTACTGGC | CGGAAAGCGC | CGCTGTGGCT | GAGAGCGAAG | 300 |
| TTTCAGAGAC | TCTTATTTAA | ACTGGGTTGT | TACATTCAAA | AGAACTGCGG | CAAGTTTTTG | 360 |
| GTTGTGGGTC | TCCTCATATT | TGGGGCCTTC | GCTGTGGGAT | TAAAGGCAGC | TAATCTCGAG | 420 |
| ACCAACGTGG | AGGAGCTGTG | GGTGGAAGTT | GGTGGACGAG | TGAGTCGAGA | ATTAAATTAT | 480 |

-continued

| | | | | | | |
|---|---|---|---|---|---|---|
| ACCCGTCAGA | AGATAGGAGA | AGAGGCTATG | TTTAATCCTC | AACTCATGAT | ACAGACTCCA | 540 |
| AAAGAAGAAG | GCGCTAATGT | TCTGACCACA | GAGGCTCTCC | TGCAACACCT | GGACTCAGCA | 600 |
| CTCCAGGCCA | GTCGTGTGCA | CGTCTACATG | TATAACAGGC | AATGGAAGTT | GGAACATTTG | 660 |
| TGCTACAAAT | CAGGGGAACT | TATCACGGAG | ACAGGTTACA | TGGATCAGAT | AATAGAATAC | 720 |
| CTTTACCCTT | GCTTAATCAT | TACACCTTTG | GACTGCTTCT | GGGAAGGGGC | AAAGCTACAG | 780 |
| TCCGGGACAG | CATACCTCCT | AGGTAAGCCT | CCTTTACGGT | GGACAAACTT | TGACCCCTTG | 840 |
| GAATTCCTAG | AAGAGTTAAA | GAAAATAAAC | TACCAAGTGG | ACAGCTGGGA | GGAAATGCTG | 900 |
| AATAAAGCCG | AAGTTGGCCA | TGGGTACATG | GACCGGCCTT | GCCTCAACCC | AGCCGACCCA | 960 |
| GATTGCCCTG | CCACAGCCCC | TAACAAAAT | TCAACCAAAC | CTCTTGATGT | GGCCCTTGTT | 1020 |
| TTGAATGGTG | GATGTCAAGG | TTTATCCAGG | AAGTATATGC | ATTGGCAGGA | GGAGTTGATT | 1080 |
| GTGGGTGGTA | CCGTCAAGAA | TGCCACTGGA | AAACTTGTCA | GCGCTCACGC | CCTGCAAACC | 1140 |
| ATGTTCCAGT | TAATGACTCC | CAAGCAAATG | TATGAACACT | TCAGGGGCTA | CGACTATGTC | 1200 |
| TCTCACATCA | ACTGGAATGA | AGACAGGGCA | GCCGCCATCC | TGGAGGCCTG | GCAGAGGACT | 1260 |
| TACGTGGAGG | TGGTTCATCA | AAGTGTCGCC | CCAAACTCCA | CTCAAAAGGT | GCTTCCCTTC | 1320 |
| ACAACCACGA | CCCTGGACGA | CATCCTAAAA | TCCTTCTCTG | ATGTCAGTGT | CATCCGAGTG | 1380 |
| GCCAGCGGCT | ACCTACTGAT | GCTTGCCTAT | GCCTGTTTAA | CCATGCTGCG | CTGGGACTGC | 1440 |
| TCCAAGTCCC | AGGGTGCCGT | GGGGCTGGCT | GGCGTCCTGT | TGGTTGCGCT | GTCAGTGGCT | 1500 |
| GCAGGATTGG | GCCTCTGCTC | CTTGATTGGC | ATTTCTTTTA | ATGCTGCGAC | AACTCAGGTT | 1560 |
| TTGCCGTTTC | TTGCTCTTGG | TGTTGGTGTG | GATGATGTCT | TCCTCCTGGC | CCATGCATTC | 1620 |
| AGTGAAACAG | GACAGAATAA | GAGGATTCCA | TTTGAGGACA | GGACTGGGGA | GTGCCTCAAG | 1680 |
| CGCACCGGAG | CCAGCGTGGC | CCTCACCTCC | ATCAGCAATG | TCACCGCCTT | CTTCATGGCC | 1740 |
| GCATTGATCC | CTATCCCTGC | CCTGCGAGCG | TTCTCCCTCC | AGGCTGCTGT | GGTGGTGGTA | 1800 |
| TTCAATTTTG | CTATGGTTCT | GCTCATTTTT | CCTGCAATTC | TCAGCATGGA | TTTATACAGA | 1860 |
| CGTGAGGACA | GAAGATTGGA | TATTTCTGC | TGTTTCACAA | GCCCCTGTGT | CAGCAGGGTG | 1920 |
| ATTCAAGTTG | AGCCACAGGC | CTACACAGAG | CCTCACAGTA | ACACCCGGTA | CAGCCCCCCA | 1980 |
| CCCCCATACA | CCAGCCACAG | CTTCGCCCAC | GAAACCCATA | TCACTATGCA | GTCCACCGTT | 2040 |
| CAGCTCCGCA | CAGAGTATGA | CCCTCACACG | CACGTGTACT | ACACCACCGC | CGAGCCACGC | 2100 |
| TCTGAGATCT | CTGTACAGCC | TGTTACCGTC | ACCCAGGACA | ACCTCAGCTG | TCAGAGTCCC | 2160 |
| GAGAGCACCA | GCTCTACCAG | GGACCTGCTC | TCCCAGTTCT | CAGACTCCAG | CCTCCACTGC | 2220 |
| CTCGAGCCCC | CCTGCACCAA | GTGGACACTC | TCTTCGTTTG | CAGAGAAGCA | CTATGCTCCT | 2280 |
| TTCCTCCTGA | AACCCAAAGC | CAAGGTTGTG | GTAATCCTTC | TTTTCCTGGG | CTTGCTGGGG | 2340 |
| GTCAGCCTTT | ATGGGACCAC | CCGAGTGAGA | GACGGGCTGG | ACCTCACGGA | CATTGTTCCC | 2400 |
| CGGGAAACCA | GAGAATATGA | CTTCATAGCT | GCCCAGTTCA | AGTACTTCTC | TTTCTACAAC | 2460 |
| ATGTATATAG | TCACCCAGAA | AGCAGACTAC | CCGAATATCC | AGCACCTACT | TTACGACCTT | 2520 |
| CATAAGAGTT | TCAGCAATGT | GAAGTATGTC | ATGCTGGAGG | AGAACAAGCA | ACTTCCCCAA | 2580 |
| ATGTGGCTGC | ACTACTTTAG | AGACTGGCTT | CAAGGACTTC | AGGATGCATT | TGACAGTGAC | 2640 |
| TGGGAAACTG | GGAGGATCAT | GCCAAACAAT | TATAAAAATG | GATCAGATGA | CGGGGTCCTC | 2700 |
| GCTTACAAAC | TCCTGGTGCA | GACTGGCAGC | CGAGACAAGC | CCATCGACAT | TAGTCAGTTG | 2760 |
| ACTAAACAGC | GTCTGGTAGA | CGCAGATGGC | ATCATTAATC | CGAGCGCTTT | CTACATCTAC | 2820 |
| CTGACCGCTT | GGGTCAGCAA | CGACCCTGTA | GCTTACGCTG | CCTCCCAGGC | CAACATCCGG | 2880 |

| | | | | | | |
|---|---|---|---|---|---|---|
| CCTCACCGGC | CGGAGTGGGT | CCATGACAAA | GCCGACTACA | TGCCAGAGAC | CAGGCTGAGA | 2940 |
| ATCCCAGCAG | CAGAGCCCAT | CGAGTACGCT | CAGTTCCCTT | TCTACCTCAA | CGGCCTACGA | 3000 |
| GACACCTCAG | ACTTTGTGGA | AGCCATAGAA | AAAGTGAGAG | TCATCTGTAA | CAACTATACG | 3060 |
| AGCCTGGGAC | TGTCCAGCTA | CCCCAATGGC | TACCCCTTCC | TGTTCTGGGA | GCAATACATC | 3120 |
| AGCCTGCGCC | ACTGGCTGCT | GCTATCCATC | AGCGTGGTGC | TGGCCTGCAC | GTTTCTAGTG | 3180 |
| TGCGCAGTCT | TCCTCCTGAA | CCCCTGGACG | GCCGGGATCA | TTGTCATGGT | CCTGGCTCTG | 3240 |
| ATGACCGTTG | AGCTCTTTGG | CATGATGGGC | CTCATTGGGA | TCAAGCTGAG | TGCTGTGCCT | 3300 |
| GTGGTCATCC | TGATTGCATC | TGTTGGCATC | GGAGTGGAGT | TCACCGTCCA | CGTGGCTTTG | 3360 |
| GCCTTTCTGA | CAGCCATTGG | GGACAAGAAC | CACAGGGCTA | TGCTCGCTCT | GGAACACATG | 3420 |
| TTTGCTCCCG | TTCTGGACGG | TGCTGTGTCC | ACTCTGCTGG | GTGTACTGAT | GCTTGCAGGG | 3480 |
| TCCGAATTTG | ATTTCATTGT | CAGATACTTC | TTTGCCGTCC | TGGCCATTCT | CACCGTCTTG | 3540 |
| GGGGTTCTCA | ATGGACTGGT | TCTGCTGCCT | GTCCTCTTAT | CCTTCTTTGG | ACCGTGTCCT | 3600 |
| GAGGTGTCTC | CAGCCAATGG | CCTAAACCGA | CTGCCCACTC | CTTCGCCTGA | GCCGCCTCCA | 3660 |
| AGTGTCGTCC | GGTTTGCCGT | GCCTCCTGGT | CACACGAACA | ATGGGTCTGA | TTCCTCCGAC | 3720 |
| TCGGAGTACA | GCTCTCAGAC | CACGGTGTCT | GGCATCAGTG | AGGAGCTCAG | GCAATACGAA | 3780 |
| GCACAGCAGG | GTGCCGGAGG | CCCTGCCCAC | CAAGTGATTG | TGGAAGCCAC | AGAAAACCCT | 3840 |
| GTCTTTGCCC | GGTCCACTGT | GGTCCATCCG | GACTCCAGAC | ATCAGCCTCC | CTTGACCCCT | 3900 |
| CGGCAACAGC | CCCACCTGGA | CTCTGGCTCC | TTGTCCCCTG | GACGGCAAGG | CCAGCAGCCT | 3960 |
| CGAAGGGATC | CCCCTAGAGA | AGGCTTGCGG | CCACCCCCCT | ACAGACCGCG | CAGAGACGCT | 4020 |
| TTTGAAATTT | CTACTGAAGG | GCATTCTGGC | CCTAGCAATA | GGGACCGCTC | AGGGCCCCGT | 4080 |
| GGGGCCCGTT | CTCACAACCC | TCGGAACCCA | ACGTCCACCG | CCATGGGCAG | CTCTGTGCCC | 4140 |
| AGCTACTGCC | AGCCCATCAC | CACTGTGACG | GCTTCTGCTT | CGGTGACTGT | TGCTGTGCAT | 4200 |
| CCCCCGCCTG | GACCTGGGCG | CAACCCCCGA | GGGGGGCCCT | GTCCAGGCTA | TGAGAGCTAC | 4260 |
| CCTGAGACTG | ATCACGGGGT | ATTTGAGGAT | CCTCATGTGC | CTTTTCATGT | CAGGTGTGAG | 4320 |
| AGGAGGGACT | CAAAGGTGGA | GGTCATAGAG | CTACAGGACG | TGGAATGTGA | GGAGAGGCCG | 4380 |
| TGGGGGAGCA | GCTCCAACTG | AGGGTAATTA | AAATCTGAAG | CAAAGAGGCC | AAAGATTGGA | 4440 |
| AAGCCCCGCC | CCCACCTCTT | TCCAGAACTG | CTTGAAGAGA | ACTGCTTGGA | ATTATGGGAA | 4500 |
| GGCAGTTCAT | TGTTACTGTA | ACTGATTGTA | TTATTKKGTG | AAATATTTCT | ATAAATATTT | 4560 |
| AARAGGTGTA | CACATGTAAT | ATACATGGAA | ATGCTGTACA | GTCTATTTCC | TGGGGCCTCT | 4620 |
| CCACTCCTGC | CCCAGAGTGG | GGAGACCACA | GGGGCCCTTT | CCCCTGTGTA | CATTGGTCTC | 4680 |
| TGTGCCACAA | CCAAGCTTAA | CTTAGTTTTA | AAAAAAATCT | CCCAGCATAT | GTCGCTGCTG | 4740 |
| CTTAAATATT | GTATAATTTA | CTTGTATAAT | TCTATGCAAA | TATTGCTTAT | GTAATAGGAT | 4800 |
| TATTTGTAAA | GGTTTCTGTT | TAAAATATTT | TAAATTTGCA | TATCACAACC | CTGTGGTAGG | 4860 |
| ATGAATTGTT | ACTGTTAACT | TTTGAACACG | CTATGCGTGG | TAATTGTTTA | ACGAGCAGAC | 4920 |
| ATGAAGAAAA | CAGGTTAATC | CCAGTGGCTT | CTCTAGGGGT | AGTTGTATAT | GGTTCGCATG | 4980 |
| GGTGGATGTG | TGTGTGCATG | TGACTTTCCA | ATGTACTGTA | TTGTGGTTTG | TTGTTGTTGT | 5040 |
| TGCTGTTGTT | GTTCATTTTG | GTGTTTTTGG | TTGCTTTGTA | TGATCTTAGC | TCTGGCCTAG | 5100 |
| GTGGGCTGGG | AAGGTCCAGG | TCTTTTTCTG | TCGTGATGCT | GGTGGAAAGG | TGACCCCAAT | 5160 |
| CATCTGTCCT | ATTCTCTGGG | ACTATTC | | | | 5187 |

( 2 ) INFORMATION FOR SEQ ID NO:10:

( i ) SEQUENCE CHARACTERISTICS:
        ( A ) LENGTH: 1434 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Met Ala Ser Ala Gly Asn Ala Ala Gly Ala Leu Gly Arg Gln Ala Gly
 1               5                  10                  15

Gly Gly Arg Arg Arg Arg Thr Gly Gly Pro His Arg Ala Ala Pro Asp
            20                  25                  30

Arg Asp Tyr Leu His Arg Pro Ser Tyr Cys Asp Ala Ala Phe Ala Leu
        35                  40                  45

Glu Gln Ile Ser Lys Gly Lys Ala Thr Gly Arg Lys Ala Pro Leu Trp
    50                  55                  60

Leu Arg Ala Lys Phe Gln Arg Leu Leu Phe Lys Leu Gly Cys Tyr Ile
65                  70                  75                  80

Gln Lys Asn Cys Gly Lys Phe Leu Val Val Gly Leu Leu Ile Phe Gly
                85                  90                  95

Ala Phe Ala Val Gly Leu Lys Ala Ala Asn Leu Glu Thr Asn Val Glu
            100                 105                 110

Glu Leu Trp Val Glu Val Gly Gly Arg Val Ser Arg Glu Leu Asn Tyr
        115                 120                 125

Thr Arg Gln Lys Ile Gly Glu Glu Ala Met Phe Asn Pro Gln Leu Met
    130                 135                 140

Ile Gln Thr Pro Lys Glu Glu Gly Ala Asn Val Leu Thr Thr Glu Ala
145                 150                 155                 160

Leu Leu Gln His Leu Asp Ser Ala Leu Gln Ala Ser Arg Val His Val
                165                 170                 175

Tyr Met Tyr Asn Arg Gln Trp Lys Leu Glu His Leu Cys Tyr Lys Ser
            180                 185                 190

Gly Glu Leu Ile Thr Glu Thr Gly Tyr Met Asp Gln Ile Ile Glu Tyr
        195                 200                 205

Leu Tyr Pro Cys Leu Ile Ile Thr Pro Leu Asp Cys Phe Trp Glu Gly
    210                 215                 220

Ala Lys Leu Gln Ser Gly Thr Ala Tyr Leu Leu Gly Lys Pro Pro Leu
225                 230                 235                 240

Arg Trp Thr Asn Phe Asp Pro Leu Glu Phe Leu Glu Glu Leu Lys Lys
                245                 250                 255

Ile Asn Tyr Gln Val Asp Ser Trp Glu Glu Met Leu Asn Lys Ala Glu
            260                 265                 270

Val Gly His Gly Tyr Met Asp Arg Pro Cys Leu Asn Pro Ala Asp Pro
        275                 280                 285

Asp Cys Pro Ala Thr Ala Pro Asn Lys Asn Ser Thr Lys Pro Leu Asp
    290                 295                 300

Val Ala Leu Val Leu Asn Gly Gly Cys Gln Gly Leu Ser Arg Lys Tyr
305                 310                 315                 320

Met His Trp Gln Glu Glu Leu Ile Val Gly Gly Thr Val Lys Asn Ala
                325                 330                 335

Thr Gly Lys Leu Val Ser Ala His Ala Leu Gln Thr Met Phe Gln Leu
            340                 345                 350

Met Thr Pro Lys Gln Met Tyr Glu His Phe Arg Gly Tyr Asp Tyr Val
        355                 360                 365
```

| | | | | | | | | | | | | | | |
|---|---|---|---|---|---|---|---|---|---|---|---|---|---|---|
| Ser | His | Ile | Asn | Trp | Asn | Glu | Asp | Arg | Ala | Ala | Ile | Leu | Glu | Ala |
| | 370 | | | | 375 | | | | | 380 | | | | |
| Trp | Gln | Arg | Thr | Tyr | Val | Glu | Val | Val | His | Gln | Ser | Val | Ala | Pro | Asn |
| 385 | | | | | 390 | | | | | 395 | | | | | 400 |
| Ser | Thr | Gln | Lys | Val | Leu | Pro | Phe | Thr | Thr | Thr | Leu | Asp | Asp | Ile |
| | | | | 405 | | | | | 410 | | | | | 415 |
| Leu | Lys | Ser | Phe | Ser | Asp | Val | Ser | Val | Ile | Arg | Val | Ala | Ser | Gly | Tyr |
| | | | 420 | | | | | 425 | | | | | 430 | |
| Leu | Leu | Met | Leu | Ala | Tyr | Ala | Cys | Leu | Thr | Met | Leu | Arg | Trp | Asp | Cys |
| | | 435 | | | | | 440 | | | | | 445 | | | |
| Ser | Lys | Ser | Gln | Gly | Ala | Val | Gly | Leu | Ala | Gly | Val | Leu | Leu | Val | Ala |
| | 450 | | | | | 455 | | | | | 460 | | | | |
| Leu | Ser | Val | Ala | Ala | Gly | Leu | Gly | Leu | Cys | Ser | Leu | Ile | Gly | Ile | Ser |
| 465 | | | | | 470 | | | | | 475 | | | | | 480 |
| Phe | Asn | Ala | Ala | Thr | Thr | Gln | Val | Leu | Pro | Phe | Leu | Ala | Leu | Gly | Val |
| | | | | 485 | | | | | 490 | | | | | 495 | |
| Gly | Val | Asp | Asp | Val | Phe | Leu | Leu | Ala | His | Ala | Phe | Ser | Glu | Thr | Gly |
| | | | 500 | | | | | 505 | | | | | 510 | | |
| Gln | Asn | Lys | Arg | Ile | Pro | Phe | Glu | Asp | Arg | Thr | Gly | Glu | Cys | Leu | Lys |
| | | | 515 | | | | | 520 | | | | | 525 | | |
| Arg | Thr | Gly | Ala | Ser | Val | Ala | Leu | Thr | Ser | Ile | Ser | Asn | Val | Thr | Ala |
| | 530 | | | | | 535 | | | | | 540 | | | | |
| Phe | Phe | Met | Ala | Ala | Leu | Ile | Pro | Ile | Pro | Ala | Leu | Arg | Ala | Phe | Ser |
| 545 | | | | | 550 | | | | | 555 | | | | | 560 |
| Leu | Gln | Ala | Ala | Val | Val | Val | Val | Phe | Asn | Phe | Ala | Met | Val | Leu | Leu |
| | | | | 565 | | | | | 570 | | | | | 575 | |
| Ile | Phe | Pro | Ala | Ile | Leu | Ser | Met | Asp | Leu | Tyr | Arg | Arg | Glu | Asp | Arg |
| | | | 580 | | | | | 585 | | | | | 590 | | |
| Arg | Leu | Asp | Ile | Phe | Cys | Cys | Phe | Thr | Ser | Pro | Cys | Val | Ser | Arg | Val |
| | | 595 | | | | | 600 | | | | | 605 | | | |
| Ile | Gln | Val | Glu | Pro | Gln | Ala | Tyr | Thr | Glu | Pro | His | Ser | Asn | Thr | Arg |
| | 610 | | | | | 615 | | | | | 620 | | | | |
| Tyr | Ser | Pro | Pro | Pro | Pro | Tyr | Thr | Ser | His | Ser | Phe | Ala | His | Glu | Thr |
| 625 | | | | | 630 | | | | | 635 | | | | | 640 |
| His | Ile | Thr | Met | Gln | Ser | Thr | Val | Gln | Leu | Arg | Thr | Glu | Tyr | Asp | Pro |
| | | | | 645 | | | | | 650 | | | | | 655 | |
| His | Thr | His | Val | Tyr | Tyr | Thr | Thr | Ala | Glu | Pro | Arg | Ser | Glu | Ile | Ser |
| | | | 660 | | | | | 665 | | | | | 670 | | |
| Val | Gln | Pro | Val | Thr | Val | Thr | Gln | Asp | Asn | Leu | Ser | Cys | Gln | Ser | Pro |
| | | 675 | | | | | 680 | | | | | 685 | | | |
| Glu | Ser | Thr | Ser | Ser | Thr | Arg | Asp | Leu | Leu | Ser | Gln | Phe | Ser | Asp | Ser |
| | 690 | | | | | 695 | | | | | 700 | | | | |
| Ser | Leu | His | Cys | Leu | Glu | Pro | Pro | Cys | Thr | Lys | Trp | Thr | Leu | Ser | Ser |
| 705 | | | | | 710 | | | | | 715 | | | | | 720 |
| Phe | Ala | Glu | Lys | His | Tyr | Ala | Pro | Phe | Leu | Leu | Lys | Pro | Lys | Ala | Lys |
| | | | | 725 | | | | | 730 | | | | | 735 | |
| Val | Val | Val | Ile | Leu | Leu | Phe | Leu | Gly | Leu | Leu | Gly | Val | Ser | Leu | Tyr |
| | | | 740 | | | | | 745 | | | | | 750 | | |
| Gly | Thr | Thr | Arg | Val | Arg | Asp | Gly | Leu | Asp | Leu | Thr | Asp | Ile | Val | Pro |
| | | 755 | | | | | 760 | | | | | 765 | | | |
| Arg | Glu | Thr | Arg | Glu | Tyr | Asp | Phe | Ile | Ala | Ala | Gln | Phe | Lys | Tyr | Phe |
| | 770 | | | | | 775 | | | | | 780 | | | | |
| Ser | Phe | Tyr | Asn | Met | Tyr | Ile | Val | Thr | Gln | Lys | Ala | Asp | Tyr | Pro | Asn |

```
                785                     790                      795                          800

Ile  Gln  His  Leu  Leu  Tyr  Asp  Leu  His  Lys  Ser  Phe  Ser  Asn  Val  Lys
                         805                      810                           815

Tyr  Val  Met  Leu  Glu  Glu  Asn  Lys  Gln  Leu  Pro  Gln  Met  Trp  Leu  His
                         820                      825                     830

Tyr  Phe  Arg  Asp  Trp  Leu  Gln  Gly  Leu  Gln  Asp  Ala  Phe  Asp  Ser  Asp
                    835                      840                     845

Trp  Glu  Thr  Gly  Arg  Ile  Met  Pro  Asn  Asn  Tyr  Lys  Asn  Gly  Ser  Asp
     850                           855                      860

Asp  Gly  Val  Leu  Ala  Tyr  Lys  Leu  Leu  Val  Gln  Thr  Gly  Ser  Arg  Asp
     865                      870                      875                          880

Lys  Pro  Ile  Asp  Ile  Ser  Gln  Leu  Thr  Lys  Gln  Arg  Leu  Val  Asp  Ala
                         885                      890                          895

Asp  Gly  Ile  Ile  Asn  Pro  Ser  Ala  Phe  Tyr  Ile  Tyr  Leu  Thr  Ala  Trp
                    900                      905                      910

Val  Ser  Asn  Asp  Pro  Val  Ala  Tyr  Ala  Ala  Ser  Gln  Ala  Asn  Ile  Arg
                    915                      920                      925

Pro  His  Arg  Pro  Glu  Trp  Val  His  Asp  Lys  Ala  Asp  Tyr  Met  Pro  Glu
          930                          935                      940

Thr  Arg  Leu  Arg  Ile  Pro  Ala  Ala  Glu  Pro  Ile  Glu  Tyr  Ala  Gln  Phe
     945                      950                      955                          960

Pro  Phe  Tyr  Leu  Asn  Gly  Leu  Arg  Asp  Thr  Ser  Asp  Phe  Val  Glu  Ala
                         965                      970                          975

Ile  Glu  Lys  Val  Arg  Val  Ile  Cys  Asn  Asn  Tyr  Thr  Ser  Leu  Gly  Leu
                    980                      985                          990

Ser  Ser  Tyr  Pro  Asn  Gly  Tyr  Pro  Phe  Leu  Phe  Trp  Glu  Gln  Tyr  Ile
               995                     1000                     1005

Ser  Leu  Arg  His  Trp  Leu  Leu  Leu  Ser  Ile  Ser  Val  Val  Leu  Ala  Cys
               1010                          1015                     1020

Thr  Phe  Leu  Val  Cys  Ala  Val  Phe  Leu  Leu  Asn  Pro  Trp  Thr  Ala  Gly
     1025                          1030                     1035                         1040

Ile  Ile  Val  Met  Val  Leu  Ala  Leu  Met  Thr  Val  Glu  Leu  Phe  Gly  Met
                         1045                     1050                          1055

Met  Gly  Leu  Ile  Gly  Ile  Lys  Leu  Ser  Ala  Val  Pro  Val  Val  Ile  Leu
                         1060                     1065                     1070

Ile  Ala  Ser  Val  Gly  Ile  Gly  Val  Glu  Phe  Thr  Val  His  Val  Ala  Leu
                    1075                          1080                     1085

Ala  Phe  Leu  Thr  Ala  Ile  Gly  Asp  Lys  Asn  His  Arg  Ala  Met  Leu  Ala
          1090                          1095                     1100

Leu  Glu  His  Met  Phe  Ala  Pro  Val  Leu  Asp  Gly  Ala  Val  Ser  Thr  Leu
     1105                          1110                     1115                         1120

Leu  Gly  Val  Leu  Met  Leu  Ala  Gly  Ser  Glu  Phe  Asp  Phe  Ile  Val  Arg
                         1125                     1130                          1135

Tyr  Phe  Phe  Ala  Val  Leu  Ala  Ile  Leu  Thr  Val  Leu  Gly  Val  Leu  Asn
                    1140                          1145                          1150

Gly  Leu  Val  Leu  Leu  Pro  Val  Leu  Leu  Ser  Phe  Phe  Gly  Pro  Cys  Pro
                    1155                          1160                     1165

Glu  Val  Ser  Pro  Ala  Asn  Gly  Leu  Asn  Arg  Leu  Pro  Thr  Pro  Ser  Pro
          1170                          1175                     1180

Glu  Pro  Pro  Pro  Ser  Val  Val  Arg  Phe  Ala  Val  Pro  Pro  Gly  His  Thr
     1185                          1190                     1195                         1200

Asn  Asn  Gly  Ser  Asp  Ser  Ser  Asp  Ser  Glu  Tyr  Ser  Ser  Gln  Thr  Thr
                         1205                     1210                          1215
```

Val Ser Gly Ile Ser Glu Glu Leu Arg Gln Tyr Glu Ala Gln Gln Gly
            1220                1225                1230

Ala Gly Gly Pro Ala His Gln Val Ile Val Glu Ala Thr Glu Asn Pro
            1235                1240                1245

Val Phe Ala Arg Ser Thr Val His Pro Asp Ser Arg His Gln Pro
            1250                1255                1260

Pro Leu Thr Pro Arg Gln Gln Pro His Leu Asp Ser Gly Ser Leu Ser
1265                1270                1275                1280

Pro Gly Arg Gln Gly Gln Gln Pro Arg Arg Asp Pro Pro Arg Glu Gly
            1285                1290                1295

Leu Arg Pro Pro Pro Tyr Arg Pro Arg Arg Asp Ala Phe Glu Ile Ser
            1300                1305                1310

Thr Glu Gly His Ser Gly Pro Ser Asn Arg Asp Arg Ser Gly Pro Arg
            1315                1320                1325

Gly Ala Arg Ser His Asn Pro Arg Asn Pro Thr Ser Thr Ala Met Gly
            1330                1335                1340

Ser Ser Val Pro Ser Tyr Cys Gln Pro Ile Thr Thr Val Thr Ala Ser
1345                1350                1355                1360

Ala Ser Val Thr Val Ala Val His Pro Pro Gly Pro Gly Arg Asn
            1365                1370                1375

Pro Arg Gly Gly Pro Cys Pro Gly Tyr Glu Ser Tyr Pro Glu Thr Asp
            1380                1385                1390

His Gly Val Phe Glu Asp Pro His Val Pro Phe His Val Arg Cys Glu
            1395                1400                1405

Arg Arg Asp Ser Lys Val Glu Val Ile Glu Leu Gln Asp Val Glu Cys
            1410                1415                1420

Glu Glu Arg Pro Trp Gly Ser Ser Ser Asn
1425                1430

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Ile Ile Thr Pro Leu Asp Cys Phe Trp Glu Gly
1               5                   10

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Leu Ile Val Gly Gly
1               5

( 2 ) INFORMATION FOR SEQ ID NO:13:

( i ) SEQUENCE CHARACTERISTICS:
        ( A ) LENGTH: 7 amino acids
        ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:13:

Pro Phe Phe Trp Glu Gln Tyr
1               5

( 2 ) INFORMATION FOR SEQ ID NO:14:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "primer"

( x i ) SEQUENCE DESCRIPTION: SEQ ID NO:14:

GGACGAATTC AARGTNCAYC ARYTNTGG                28

( 2 ) INFORMATION FOR SEQ ID NO:15:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "primer"

( x i ) SEQUENCE DESCRIPTION: SEQ ID NO:15:

GGACGAATTC CYTCCCARAA RCANTC                  26

( 2 ) INFORMATION FOR SEQ ID NO:16:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "primer"

( x i ) SEQUENCE DESCRIPTION: SEQ ID NO:16:

GGACGAATTC YTNGANTGYT TYTGGGA                 27

( 2 ) INFORMATION FOR SEQ ID NO:17:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "primer"

( x i ) SEQUENCE DESCRIPTION: SEQ ID NO:17:

CATACCAGCC AAGCTTGTCN GGCCARTGCA T            31

( 2 ) INFORMATION FOR SEQ ID NO:18:

( i ) SEQUENCE CHARACTERISTICS:
( A ) LENGTH: 5288 base pairs
( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:18:

| | | | | | | |
|---|---|---|---|---|---|---|
| GAATTCCGGG | GACCGCAAGG | AGTGCCGCGG | AAGCGCCCGA | AGGACAGGCT | CGCTCGGCGC | 60 |
| GCCGGCTCTC | GCTCTTCCGC | GAACTGGATG | TGGGCAGCGG | CGGCCGCAGA | GACCTCGGGA | 120 |
| CCCCCGCGCA | ATGTGGCAAT | GGAAGGCGCA | GGGTCTGACT | CCCCGGCAGC | GGCCGCGGCC | 180 |
| GCAGCGGCAG | CAGCGCCCGC | CGTGTGAGCA | GCAGCAGCGG | CTGGTCTGTC | AACCGGAGCC | 240 |
| CGAGCCCGAG | CAGCCTGCGG | CCAGCAGCGT | CCTCGCAAGC | CGAGCGCCCA | GGCGCGCCAG | 300 |
| GAGCCCGCAG | CAGCGGCAGC | AGCGCGCCGG | GCCGCCCGGG | AAGCCTCCGT | CCCCGCGGCG | 360 |
| GCGGCGGCGG | CGGCGGCGGC | AACATGGCCT | CGGCTGGTAA | CGCCGCCGAG | CCCCAGGACC | 420 |
| GCGGCGGCGG | CGGCAGCGGC | TGTATCGGTG | CCCCGGGACG | GCCGGCTGGA | GGCGGGAGGC | 480 |
| GCAGACGGAC | GGGGGGGCTG | CGCCGTGCTG | CCGCGCCGGA | CCGGGACTAT | CTGCACCGGC | 540 |
| CCAGCTACTG | CGACGCCGCC | TTCGCTCTGG | AGCAGATTTC | CAAGGGGAAG | GCTACTGGCC | 600 |
| GGAAAGCGCC | ACTGTGGCTG | AGAGCGAAGT | TTCAGAGACT | CTTATTTAAA | CTGGGTTGTT | 660 |
| ACATTCAAAA | AAACTGCGGC | AAGTTCTTGG | TTGTGGGCCT | CCTCATATTT | GGGGCCTTCG | 720 |
| CGGTGGGATT | AAAAGCAGCG | AACCTCGAGA | CCAACGTGGA | GGAGCTGTGG | GTGGAAGTTG | 780 |
| GAGGACGAGT | AAGTCGTGAA | TTAAATTATA | CTCGCCAGAA | GATTGGAGAA | GAGGCTATGT | 840 |
| TTAATCCTCA | ACTCATGATA | CAGACCCCTA | AGAAGAAGG | TGCTAATGTC | CTGACCACAG | 900 |
| AAGCGCTCCT | ACAACACCTG | GACTCGGCAC | TCCAGGCCAG | CCGTGTCCAT | GTATACATGT | 960 |
| ACAACAGGCA | GTGGAAATTG | GAACATTTGT | GTTACAAATC | AGGAGAGCTT | ATCACAGAAA | 1020 |
| CAGGTTACAT | GGATCAGATA | ATAGAATATC | TTTACCCTTG | TTTGATTATT | ACACCTTTGG | 1080 |
| ACTGCTTCTG | GGAAGGGGCG | AAATTACAGT | CTGGGACAGC | ATACCTCCTA | GGTAAACCTC | 1140 |
| CTTTGCGGTG | GACAAACTTC | GACCCTTTGG | AATTCCTGGA | AGAGTTAAAG | AAAATAAACT | 1200 |
| ATCAAGTGGA | CAGCTGGGAG | GAAATGCTGA | ATAAGGCTGA | GGTTGGTCAT | GGTTACATGG | 1260 |
| ACCGCCCCTG | CCTCAATCCG | GCCGATCCAG | ACTGCCCCGC | CACAGCCCCC | AACAAAAATT | 1320 |
| CAACCAAACC | TCTTGATATG | GCCCTTGTTT | TGAATGGTGG | ATGTCATGGC | TTATCCAGAA | 1380 |
| AGTATATGCA | CTGGCAGGAG | GAGTTGATTG | TGGGTGGCAC | AGTCAAGAAC | AGCACTGGAA | 1440 |
| AACTCGTCAG | CGCCCATGCC | CTGCAGACCA | TGTTCCAGTT | AATGACTCCC | AAGCAAATGT | 1500 |
| ACGAGCACTT | CAAGGGGTAC | GAGTATGTCT | CACACATCAA | CTGGAACGAG | GACAAAGCGG | 1560 |
| CAGCCATCCT | GGAGGCCTGG | CAGAGGACAT | ATGTGGAGGT | GGTTCATCAG | AGTGTCGCAC | 1620 |
| AGAACTCCAC | TCAAAAGGTG | CTTTCCTTCA | CCACCACGAC | CCTGGACGAC | ATCCTGAAAT | 1680 |
| CCTTCTCTGA | CGTCAGTGTC | ATCCGCGTGG | CCAGCGGCTA | CTTACTCATG | CTCGCCTATG | 1740 |
| CCTGTCTAAC | CATGCTGCGC | TGGGACTGCT | CCAAGTCCCA | GGGTGCCGTG | GGGCTGGCTG | 1800 |
| GCGTCCTGCT | GGTTGCACTG | TCAGTGGCTG | CAGGACTGGG | CCTGTGCTCA | TTGATCGGAA | 1860 |
| TTTCCTTTAA | CGCTGCAACA | ACTCAGGTTT | TGCCATTTCT | CGCTCTTGGT | GTTGGTGTGG | 1920 |
| ATGATGTTTT | TCTTCTGGCC | CACGCCTTCA | GTGAAACAGG | ACAGAATAAA | AGAATCCCTT | 1980 |
| TTGAGGACAG | GACCGGGGAG | TGCCTGAAGC | GCACAGGAGC | CAGCGTGGCC | CTCACGTCCA | 2040 |
| TCAGCAATGT | CACAGCCTTC | TTCATGGCCG | CGTTAATCCC | AATTCCCGCT | CTGCGGGCGT | 2100 |
| TCTCCCTCCA | GGCAGCGGTA | GTAGTGGTGT | TCAATTTTGC | CATGGTTCTG | CTCATTTTTC | 2160 |
| CTGCAATTCT | CAGCATGGAT | TTATATCGAC | GCGAGGACAG | GAGACTGGAT | ATTTTCTGCT | 2220 |

```
GTTTTACAAG  CCCCTGCGTC  AGCAGAGTGA  TTCAGGTTGA  ACCTCAGGCC  TACACCGACA  2280
CACACGACAA  TACCCGCTAC  AGCCCCCCAC  CTCCCTACAG  CAGCCACAGC  TTTGCCCATG  2340
AAACGCAGAT  TACCATGCAG  TCCACTGTCC  AGCTCCGCAC  GGAGTACGAC  CCCCACACGC  2400
ACGTGTACTA  CACCACCGCT  GAGCCGCGCT  CCGAGATCTC  TGTGCAGCCC  GTCACCGTGA  2460
CACAGGACAC  CCTCAGCTGC  CAGAGCCAG   AGAGCACCAG  CTCCACAAGG  GACCTGCTCT  2520
CCCAGTTCTC  CGACTCCAGC  CTCCACTGCC  TCGAGCCCCC  CTGTACGAAG  TGGACACTCT  2580
CATCTTTTGC  TGAGAAGCAC  TATGCTCCTT  TCCTCTTGAA  ACCAAAAGCC  AAGGTAGTGG  2640
TGATCTTCCT  TTTTCTGGGC  TTGCTGGGGG  TCAGCCTTTA  TGGCACCACC  CGAGTGAGAG  2700
ACGGGCTGGA  CCTTACGGAC  ATTGTACCTC  GGGAAACCAG  AGAATATGAC  TTTATTGCTG  2760
CACAATTCAA  ATACTTTTCT  TTCTACAACA  TGTATATAGT  CACCCAGAAA  GCAGACTACC  2820
CGAATATCCA  GCACTTACTT  TACGACCTAC  ACAGGAGTTT  CAGTAACGTG  AAGTATGTCA  2880
TGTTGGAAGA  AAACAAACAG  CTTCCCAAAA  TGTGGCTGCA  CTACTTCAGA  GACTGGCTTC  2940
AGGGACTTCA  GGATGCATTT  GACAGTGACT  GGGAAACCGG  GAAAATCATG  CCAAACAATT  3000
ACAAGAATGG  ATCAGACGAT  GGAGTCCTTG  CCTACAAACT  CCTGGTGCAA  ACCGGCAGCC  3060
GCGATAAGCC  CATCGACATC  AGCCAGTTGA  CTAAACAGCG  TCTGGTGGAT  GCAGATGGCA  3120
TCATTAATCC  CAGCGCTTTC  TACATCTACC  TGACGGCTTG  GGTCAGCAAC  GACCCCGTCG  3180
CGTATGCTGC  CTCCCAGGCC  AACATCCGGC  CACACCGACC  AGAATGGGTC  CACGACAAAG  3240
CCGACTACAT  GCCTGAAACA  AGGCTGAGAA  TCCCGGCAGC  AGAGCCCATC  GAGTATGCCC  3300
AGTTCCCTTT  CTACCTCAAC  GGGTTGCGGG  ACACCTCAGA  CTTTGTGGAG  GCAATTGAAA  3360
AAGTAAGGAC  CATCTGCAGC  AACTATACGA  GCCTGGGGCT  GTCCAGTTAC  CCCAACGGCT  3420
ACCCCTTCCT  CTTCTGGGAG  CAGTACATCG  GCCTCCGCCA  CTGGCTGCTG  CTGTTCATCA  3480
GCGTGGTGTT  GGCCTGCACA  TTCCTCGTGT  GCGCTGTCTT  CCTTCTGAAC  CCCTGGACGG  3540
CCGGGATCAT  TGTGATGGTC  CTGGCGCTGA  TGACGGTCGA  GCTGTTCGGC  ATGATGGGCC  3600
TCATCGGAAT  CAAGCTCAGT  GCCGTGCCCG  TGGTCATCCT  GATCGCTTCT  GTTGGCATAG  3660
GAGTGGAGTT  CACCGTTCAC  GTTGCTTTGG  CCTTTCTGAC  GGCCATCGGC  GACAAGAACC  3720
GCAGGGCTGT  GCTTGCCCTG  GAGCACATGT  TTGCACCCGT  CCTGGATGGC  GCCGTGTCCA  3780
CTCTGCTGGG  AGTGCTGATG  CTGGCGGGAT  CTGAGTTCGA  CTTCATTGTC  AGGTATTTCT  3840
TTGCTGTGCT  GGCGATCCTC  ACCATCCTCG  GCGTTCTCAA  TGGGCTGGTT  TTGCTTCCCG  3900
TGCTTTTGTC  TTTCTTTGGA  CCATATCCTG  AGGTGTCTCC  AGCCAACGGC  TTGAACCGCC  3960
TGCCCACACC  CTCCCCTGAG  CCACCCCCA   GCGTGGTCCG  CTTCGCCATG  CCGCCCGGCC  4020
ACACGCACAG  CGGGTCTGAT  TCCTCCGACT  CGGAGTATAG  TTCCCAGACG  ACAGTGTCAG  4080
GCCTCAGCGA  GGAGCTTCGG  CACTACGAGG  CCCAGCAGGG  CGCGGGAGGC  CCTGCCCACC  4140
AAGTGATCGT  GGAAGCCACA  GAAAACCCCG  TCTTCGCCCA  CTCCACTGTG  GTCCATCCCG  4200
AATCCAGGCA  TCACCCACCC  TCGAACCCGA  GACAGCAGCC  CCACCTGGAC  TCAGGGTCCC  4260
TGCCTCCCGG  ACGGCAAGGC  CAGCAGCCCC  GCAGGGACCC  CCCCAGAGAA  GGCTTGTGGC  4320
CACCCCTCTA  CAGACCGCGC  AGAGACGCTT  TTGAAATTTC  TACTGAAGGG  CATTCTGGCC  4380
CTAGCAATAG  GGCCCGCTGG  GGCCCTCGCG  GGCCCGTTC   TCACAACCCT  CGGAACCCAG  4440
CGTCCACTGC  CATGGGCAGC  TCCGTGCCCG  GCTACTGCCA  GCCCATCACC  ACTGTGACGG  4500
CTTCTGCCTC  CGTGACTGTC  GCCGTGCACC  CGCCGCCTGT  CCCTGGGCCT  GGGCGGAACC  4560
CCCGAGGGGG  ACTCTGCCCA  GGCTACCCTG  AGACTGACCA  CGGCCTGTTT  GAGGACCCCC  4620
```

```
ACGTGCCTTT CCACGTCCGG TGTGAGAGGA GGGATTCGAA GGTGGAAGTC ATTGAGCTGC    4680

AGGACGTGGA ATGCGAGGAG AGGCCCCGGG GAAGCAGCTC CAACTGAGGG TGATTAAAAT    4740

CTGAAGCAAA GAGGCCAAAG ATTGGAAACC CCCCACCCCC ACCTCTTTCC AGAACTGCTT    4800

GAAGAGAACT GGTTGGAGTT ATGGAAAAGA TGCCCTGTGC CAGGACAGCA GTTCATTGTT    4860

ACTGTAACCG ATTGTATTAT TTTGTTAAAT ATTTCTATAA ATATTTAAGA GATGTACACA    4920

TGTGTAATAT AGGAAGGAAG GATGTAAAGT GGTATGATCT GGGGCTTCTC CACTCCTGCC    4980

CCAGAGTGTG GAGGCCACAG TGGGGCCTCT CCGTATTTGT GCATGGGCT CCGTGCCACA     5040

ACCAAGCTTC ATTAGTCTTA AATTTCAGCA TATGTTGCTG CTGCTTAAAT ATTGTATAAT    5100

TTACTTGTAT AATTCTATGC AAATATTGCT TATGTAATAG GATTATTTTG TAAAGGTTTC    5160

TGTTTAAAAT ATTTTAAATT TGCATATCAC AACCCTGTGG TAGTATGAAA TGTTACTGTT    5220

AACTTTCAAA CACGCTATGC GTGATAATTT TTTTGTTTAA TGAGCAGATA TGAAGAAAGC    5280

CCGGAATT                                                            5288
```

( 2 ) INFORMATION FOR SEQ ID NO:19:

( i ) SEQUENCE CHARACTERISTICS:
        ( A ) LENGTH: 1447 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

```
Met Ala Ser Ala Gly Asn Ala Ala Glu Pro Gln Asp Arg Gly Gly Gly
 1               5                  10                  15

Gly Ser Gly Cys Ile Gly Ala Pro Gly Arg Pro Ala Gly Gly Gly Arg
                20                  25                  30

Arg Arg Arg Thr Gly Gly Leu Arg Arg Ala Ala Ala Pro Asp Arg Asp
                35                  40                  45

Tyr Leu His Arg Pro Ser Tyr Cys Asp Ala Ala Phe Ala Leu Glu Gln
 50                  55                  60

Ile Ser Lys Gly Lys Ala Thr Gly Arg Lys Ala Pro Leu Trp Leu Arg
 65                  70                  75                  80

Ala Lys Phe Gln Arg Leu Leu Phe Lys Leu Gly Cys Tyr Ile Gln Lys
                85                  90                  95

Asn Cys Gly Lys Phe Leu Val Val Gly Leu Leu Ile Phe Gly Ala Phe
                100                 105                 110

Ala Val Gly Leu Lys Ala Ala Asn Leu Glu Thr Asn Val Glu Glu Leu
                115                 120                 125

Trp Val Glu Val Gly Gly Arg Val Ser Arg Glu Leu Asn Tyr Thr Arg
        130                 135                 140

Gln Lys Ile Gly Glu Glu Ala Met Phe Asn Pro Gln Leu Met Ile Gln
145                 150                 155                 160

Thr Pro Lys Glu Glu Gly Ala Asn Val Leu Thr Thr Glu Ala Leu Leu
                165                 170                 175

Gln His Leu Asp Ser Ala Leu Gln Ala Ser Arg Val His Val Tyr Met
                180                 185                 190

Tyr Asn Arg Gln Trp Lys Leu Glu His Leu Cys Tyr Lys Ser Gly Glu
            195                 200                 205

Leu Ile Thr Glu Thr Gly Tyr Met Asp Gln Ile Ile Glu Tyr Leu Tyr
        210                 215                 220
```

```
Pro  Cys  Leu  Ile  Ile  Thr  Pro  Leu  Asp  Cys  Phe  Trp  Glu  Gly  Ala  Lys
225                 230                 235                      240

Leu  Gln  Ser  Gly  Thr  Ala  Tyr  Leu  Leu  Gly  Lys  Pro  Pro  Leu  Arg  Trp
                    245                 250                      255

Thr  Asn  Phe  Asp  Pro  Leu  Glu  Phe  Leu  Glu  Glu  Leu  Lys  Lys  Ile  Asn
               260                 265                      270

Tyr  Gln  Val  Asp  Ser  Trp  Glu  Met  Leu  Asn  Lys  Ala  Glu  Val  Gly
          275                      280                 285

His  Gly  Tyr  Met  Asp  Arg  Pro  Cys  Leu  Asn  Pro  Ala  Asp  Pro  Asp  Cys
     290                 295                      300

Pro  Ala  Thr  Ala  Pro  Asn  Lys  Asn  Ser  Thr  Lys  Pro  Leu  Asp  Met  Ala
305                      310                 315                           320

Leu  Val  Leu  Asn  Gly  Gly  Cys  His  Gly  Leu  Ser  Arg  Lys  Tyr  Met  His
                    325                 330                      335

Trp  Gln  Glu  Glu  Leu  Ile  Val  Gly  Gly  Thr  Val  Lys  Asn  Ser  Thr  Gly
               340                 345                      350

Lys  Leu  Val  Ser  Ala  His  Ala  Leu  Gln  Thr  Met  Phe  Gln  Leu  Met  Thr
               355                 360                 365

Pro  Lys  Gln  Met  Tyr  Glu  His  Phe  Lys  Gly  Tyr  Glu  Tyr  Val  Ser  His
     370                      375                 380

Ile  Asn  Trp  Asn  Glu  Asp  Lys  Ala  Ala  Ala  Ile  Leu  Glu  Ala  Trp  Gln
385                 390                      395                           400

Arg  Thr  Tyr  Val  Glu  Val  Val  His  Gln  Ser  Val  Ala  Gln  Asn  Ser  Thr
                    405                 410                      415

Gln  Lys  Val  Leu  Ser  Phe  Thr  Thr  Thr  Leu  Asp  Asp  Ile  Leu  Lys
               420                 425                 430

Ser  Phe  Ser  Asp  Val  Ser  Val  Ile  Arg  Val  Ala  Ser  Gly  Tyr  Leu  Leu
               435                 440                 445

Met  Leu  Ala  Tyr  Ala  Cys  Leu  Thr  Met  Leu  Arg  Trp  Asp  Cys  Ser  Lys
     450                      455                 460

Ser  Gln  Gly  Ala  Val  Gly  Leu  Ala  Gly  Val  Leu  Leu  Val  Ala  Leu  Ser
465                      470                 475                           480

Val  Ala  Ala  Gly  Leu  Gly  Leu  Cys  Ser  Leu  Ile  Gly  Ile  Ser  Phe  Asn
                    485                 490                      495

Ala  Ala  Thr  Thr  Gln  Val  Leu  Pro  Phe  Leu  Ala  Leu  Gly  Val  Gly  Val
               500                 505                      510

Asp  Asp  Val  Phe  Leu  Leu  Ala  His  Ala  Phe  Ser  Glu  Thr  Gly  Gln  Asn
          515                      520                 525

Lys  Arg  Ile  Pro  Phe  Glu  Asp  Arg  Thr  Gly  Glu  Cys  Leu  Lys  Arg  Thr
     530                      535                 540

Gly  Ala  Ser  Val  Ala  Leu  Thr  Ser  Ile  Ser  Asn  Val  Thr  Ala  Phe  Phe
545                      550                 555                           560

Met  Ala  Ala  Leu  Ile  Pro  Ile  Pro  Ala  Leu  Arg  Ala  Phe  Ser  Leu  Gln
                    565                 570                      575

Ala  Ala  Val  Val  Val  Phe  Asn  Phe  Ala  Met  Val  Leu  Leu  Ile  Phe
               580                 585                 590

Pro  Ala  Ile  Leu  Ser  Met  Asp  Leu  Tyr  Arg  Arg  Glu  Asp  Arg  Arg  Leu
          595                 600                      605

Asp  Ile  Phe  Cys  Cys  Phe  Thr  Ser  Pro  Cys  Val  Ser  Arg  Val  Ile  Gln
     610                 615                      620

Val  Glu  Pro  Gln  Ala  Tyr  Thr  Asp  Thr  His  Asp  Asn  Thr  Arg  Tyr  Ser
625                      630                      635                      640

Pro  Pro  Pro  Pro  Tyr  Ser  Ser  His  Ser  Phe  Ala  His  Glu  Thr  Gln  Ile
                    645                 650                      655
```

```
Thr  Met  Gln  Ser  Thr  Val  Gln  Leu  Arg  Thr  Glu  Tyr  Asp  Pro  His  Thr
          660                      665                     670

His  Val  Tyr  Tyr  Thr  Thr  Ala  Glu  Pro  Arg  Ser  Glu  Ile  Ser  Val  Gln
               675                 680                     685

Pro  Val  Thr  Val  Thr  Gln  Asp  Thr  Leu  Ser  Cys  Gln  Ser  Pro  Glu  Ser
          690                 695                     700

Thr  Ser  Ser  Thr  Arg  Asp  Leu  Leu  Ser  Gln  Phe  Ser  Asp  Ser  Ser  Leu
705                      710                     715                         720

His  Cys  Leu  Glu  Pro  Pro  Cys  Thr  Lys  Trp  Thr  Leu  Ser  Ser  Phe  Ala
                    725                     730                         735

Glu  Lys  His  Tyr  Ala  Pro  Phe  Leu  Leu  Lys  Pro  Lys  Ala  Lys  Val  Val
               740                      745                     750

Val  Ile  Phe  Leu  Phe  Leu  Gly  Leu  Leu  Gly  Val  Ser  Leu  Tyr  Gly  Thr
               755                 760                     765

Thr  Arg  Val  Arg  Asp  Gly  Leu  Asp  Leu  Thr  Asp  Ile  Val  Pro  Arg  Glu
          770                 775                     780

Thr  Arg  Glu  Tyr  Asp  Phe  Ile  Ala  Ala  Gln  Phe  Lys  Tyr  Phe  Ser  Phe
785                      790                     795                         800

Tyr  Asn  Met  Tyr  Ile  Val  Thr  Gln  Lys  Ala  Asp  Tyr  Pro  Asn  Ile  Gln
                    805                     810                         815

His  Leu  Leu  Tyr  Asp  Leu  His  Arg  Ser  Phe  Ser  Asn  Val  Lys  Tyr  Val
               820                 825                     830

Met  Leu  Glu  Glu  Asn  Lys  Gln  Leu  Pro  Lys  Met  Trp  Leu  His  Tyr  Phe
          835                      840                     845

Arg  Asp  Trp  Leu  Gln  Gly  Leu  Gln  Asp  Ala  Phe  Asp  Ser  Asp  Trp  Glu
          850                 855                     860

Thr  Gly  Lys  Ile  Met  Pro  Asn  Asn  Tyr  Lys  Asn  Gly  Ser  Asp  Asp  Gly
865                      870                     875                         880

Val  Leu  Ala  Tyr  Lys  Leu  Leu  Val  Gln  Thr  Gly  Ser  Arg  Asp  Lys  Pro
                    885                     890                         895

Ile  Asp  Ile  Ser  Gln  Leu  Thr  Lys  Gln  Arg  Leu  Val  Asp  Ala  Asp  Gly
               900                 905                     910

Ile  Ile  Asn  Pro  Ser  Ala  Phe  Tyr  Ile  Tyr  Leu  Thr  Ala  Trp  Val  Ser
          915                      920                     925

Asn  Asp  Pro  Val  Ala  Tyr  Ala  Ala  Ser  Gln  Ala  Asn  Ile  Arg  Pro  His
930                      935                     940

Arg  Pro  Glu  Trp  Val  His  Asp  Lys  Ala  Asp  Tyr  Met  Pro  Glu  Thr  Arg
945                      950                     955                         960

Leu  Arg  Ile  Pro  Ala  Ala  Glu  Pro  Ile  Glu  Tyr  Ala  Gln  Phe  Pro  Phe
                    965                     970                         975

Tyr  Leu  Asn  Gly  Leu  Arg  Asp  Thr  Ser  Asp  Phe  Val  Glu  Ala  Ile  Glu
               980                 985                     990

Lys  Val  Arg  Thr  Ile  Cys  Ser  Asn  Tyr  Thr  Ser  Leu  Gly  Leu  Ser  Ser
          995                      1000                    1005

Tyr  Pro  Asn  Gly  Tyr  Pro  Phe  Leu  Phe  Trp  Glu  Gln  Tyr  Ile  Gly  Leu
     1010                     1015                    1020

Arg  His  Trp  Leu  Leu  Leu  Phe  Ile  Ser  Val  Val  Leu  Ala  Cys  Thr  Phe
1025                     1030                    1035                        1040

Leu  Val  Cys  Ala  Val  Phe  Leu  Leu  Asn  Pro  Trp  Thr  Ala  Gly  Ile  Ile
                    1045                    1050                        1055

Val  Met  Val  Leu  Ala  Leu  Met  Thr  Val  Glu  Leu  Phe  Gly  Met  Met  Gly
                    1060                    1065                    1070

Leu  Ile  Gly  Ile  Lys  Leu  Ser  Ala  Val  Pro  Val  Val  Ile  Leu  Ile  Ala
```

-continued

```
                 1 0 7 5                          1 0 8 0                              1 0 8 5
      Ser  Val  Gly  Ile  Gly  Val  Glu  Phe  Thr  Val  His  Val  Ala  Leu  Ala  Phe
                     1 0 9 0                          1 0 9 5                          1 1 0 0
      Leu  Thr  Ala  Ile  Gly  Asp  Lys  Asn  Arg  Arg  Ala  Val  Leu  Ala  Leu  Glu
      1 1 0 5                          1 1 1 0                          1 1 1 5                     1 1 2 0
      His  Met  Phe  Ala  Pro  Val  Leu  Asp  Gly  Ala  Val  Ser  Thr  Leu  Leu  Gly
                                    1 1 2 5                          1 1 3 0                          1 1 3 5
      Val  Leu  Met  Leu  Ala  Gly  Ser  Glu  Phe  Asp  Phe  Ile  Val  Arg  Tyr  Phe
                               1 1 4 0                          1 1 4 5                          1 1 5 0
      Phe  Ala  Val  Leu  Ala  Ile  Leu  Thr  Ile  Leu  Gly  Val  Leu  Asn  Gly  Leu
                          1 1 5 5                          1 1 6 0                          1 1 6 5
      Val  Leu  Leu  Pro  Val  Leu  Leu  Ser  Phe  Phe  Gly  Pro  Tyr  Pro  Glu  Val
           1 1 7 0                          1 1 7 5                          1 1 8 0
      Ser  Pro  Ala  Asn  Gly  Leu  Asn  Arg  Leu  Pro  Thr  Pro  Ser  Pro  Glu  Pro
      1 1 8 5                          1 1 9 0                          1 1 9 5                     1 2 0 0
      Pro  Pro  Ser  Val  Val  Arg  Phe  Ala  Met  Pro  Pro  Gly  His  Thr  His  Ser
                                    1 2 0 5                          1 2 1 0                          1 2 1 5
      Gly  Ser  Asp  Ser  Ser  Asp  Ser  Glu  Tyr  Ser  Ser  Gln  Thr  Thr  Val  Ser
                               1 2 2 0                          1 2 2 5                          1 2 3 0
      Gly  Leu  Ser  Glu  Glu  Leu  Arg  His  Tyr  Glu  Ala  Gln  Gln  Gly  Ala  Gly
                     1 2 3 5                          1 2 4 0                          1 2 4 5
      Gly  Pro  Ala  His  Gln  Val  Ile  Val  Glu  Ala  Thr  Glu  Asn  Pro  Val  Phe
           1 2 5 0                          1 2 5 5                          1 2 6 0
      Ala  His  Ser  Thr  Val  Val  His  Pro  Glu  Ser  Arg  His  His  Pro  Pro  Ser
      1 2 6 5                          1 2 7 0                          1 2 7 5                     1 2 8 0
      Asn  Pro  Arg  Gln  Gln  Pro  His  Leu  Asp  Ser  Gly  Ser  Leu  Pro  Pro  Gly
                                    1 2 8 5                          1 2 9 0                          1 2 9 5
      Arg  Gln  Gly  Gln  Gln  Pro  Arg  Arg  Asp  Pro  Pro  Arg  Glu  Gly  Leu  Trp
                               1 3 0 0                          1 3 0 5                          1 3 1 0
      Pro  Pro  Leu  Tyr  Arg  Pro  Arg  Arg  Asp  Ala  Phe  Glu  Ile  Ser  Thr  Glu
                     1 3 1 5                          1 3 2 0                          1 3 2 5
      Gly  His  Ser  Gly  Pro  Ser  Asn  Arg  Ala  Arg  Trp  Gly  Pro  Arg  Gly  Ala
           1 3 3 0                          1 3 3 5                          1 3 4 0
      Arg  Ser  His  Asn  Pro  Arg  Asn  Pro  Ala  Ser  Thr  Ala  Met  Gly  Ser  Ser
      1 3 4 5                          1 3 5 0                          1 3 5 5                     1 3 6 0
      Val  Pro  Gly  Tyr  Cys  Gln  Pro  Ile  Thr  Thr  Val  Thr  Ala  Ser  Ala  Ser
                                    1 3 6 5                          1 3 7 0                          1 3 7 5
      Val  Thr  Val  Ala  Val  His  Pro  Pro  Pro  Val  Pro  Gly  Pro  Gly  Arg  Asn
                               1 3 8 0                          1 3 8 5                          1 3 9 0
      Pro  Arg  Gly  Gly  Leu  Cys  Pro  Gly  Tyr  Pro  Glu  Thr  Asp  His  Gly  Leu
                     1 3 9 5                          1 4 0 0                          1 4 0 5
      Phe  Glu  Asp  Pro  His  Val  Pro  Phe  His  Val  Arg  Cys  Glu  Arg  Arg  Asp
           1 4 1 0                          1 4 1 5                          1 4 2 0
      Ser  Lys  Val  Glu  Val  Ile  Glu  Leu  Gln  Asp  Val  Glu  Cys  Glu  Glu  Arg
      1 4 2 5                          1 4 3 0                          1 4 3 5                     1 4 4 0
      Pro  Arg  Gly  Ser  Ser  Ser  Asn
                          1 4 4 5
```

PATCHED GENES AND THEIR USE

CROSS REFERENCE TO RELATED APPLICATIONS

This application is a continuation-in-part of application Ser. No. 08/319,745, filed Oct. 7, 1994, now abandoned, the disclosure of which is herein incorporated by reference.

INTRODUCTION

1. Technical Field

The field of this invention concerns segment polarity genes and their uses.

2. Background

Segment polarity genes were discovered in flies as mutations which change the pattern of structures of the body segments. Mutations in the genes cause animals to develop the changed patterns on the surfaces of body segments, the changes affecting the pattern along the head to tail axis. For example, mutations in the gene patched cause each body segment to develop without the normal structures in the center of each segment. In their stead is a mirror image of the pattern normally found in the anterior segment. Thus cells in the center of the segment make the wrong structures, and point them in the wrong direction with reference to the over all head-to-tail polarity of the animal. About sixteen genes in the class are known. The encoded proteins include kinases, transcription factors, a cell junction protein, two secreted proteins called wingless (WG) and hedgehog (HH), a single transmembrane protein called patched (PTC), and some novel proteins not related to any known protein. All of these proteins are believed to work together in signaling pathways that inform cells about their neighbors in order to set cell fates and polarities.

Many of the segment polarity proteins of Drosophila and other invertebrates are closely related to vertebrate proteins, implying that the molecular mechanisms involved are ancient. Among the vertebrate proteins related to the fly genes are En-1 and -2, which act in vertebrate brain development and WNT-1, which is also involved in brain development, but was first found as the oncogene implicated in many cases of mouse breast cancer. In flies, the patched gene is transcribed into RNA in a complex and dynamic pattern in embryos, including fine transverse stripes in each body segment primordium. The encoded protein is predicted to contain many transmembrane domains. It has no significant similarity to any other known protein. Other proteins having large numbers of transmembrane domains include a variety of membrane receptors, channels through membranes and transporters through membranes.

The hedgehog (HH) protein of flies has been shown to have at least three vertebrate relatives: Sonic hedgehog (Shh); Indian hedgehog, and Desert hedgehog. The Shh is expressed in a group of cells at the posterior of each developing limb bud. This is exactly the same group of cells found to have an important role in signaling polarity to the developing limb. The signal appears to be graded, with cells close to the posterior source of the signal forming posterior digits and other limb structures and cells farther from the signal source forming more anterior structures. It has been known for many years that transplantation of the signaling cells, a region of the limb bud known as the "zone of polarizing activity (ZPA)" has dramatic effects on limb patterning. Implanting a second ZPA anterior to the limb bud causes a limb to develop with posterior features replacing the anterior ones (in essence little fingers instead of thumbs). Shh has been found to be the long sought ZPA signal. Cultured cells making Shh protein (SHH), when implanted into the anterior limb bud region, have the same effect as an implanted ZPA. This establishes that Shh is clearly a critical trigger of posterior limb development.

The factor in the ZPA has been thought for some time to be related to another important developmental signal that polarizes the developing spinal cord. The notochord, a rod of mesoderm that runs along the dorsal side of early vertebrate embryos, is a signal source that polarizes the neural tube along the dorsal-ventral axis. The signal causes the part of the neural tube nearest to the notochord to form floor plate, a morphologically distinct part of the neural tube. The floor plate, in turn, sends out signals to the more dorsal parts of the neural tube to further determine cell fates. The ZPA was reported to have the same signaling effect as the notochord when transplanted to be adjacent to the neural tube, suggesting the ZPA makes the same signal as the notochord. In keeping with this view, Shh was found to be produced by notochord cells and floor plate cells. Tests of extra expression of Shh in mice led to the finding of extra expression of floor plate genes in cells which would not normally turn them on. Therefore Shh appears to be a component of the signal from notochord to floor plate and from floor plate to more dorsal parts of the neural tube. Besides limb and neural tubes, vertebrate hedgehog genes are also expressed in many other tissues including, but not limited to the peripheral nervous system, brain, lung, liver, kidney, tooth primordia, genitalia, and hindgut and foregut endoderm.

PTC has been proposed as a receptor for HH protein based on genetic experiments in flies. A model for the relationship is that PTC acts through a largely unknown pathway to inactivate both its own transcription and the transcription of the wingless segment polarity gene. This model proposes that HH protein, secreted from adjacent cells, binds to the PTC receptor, inactivates it, and thereby prevents PTC from turning off its own transcription or that of wingless. A number of experiments have shown coordinate events between PTC and HH.

Relevant Literature

Descriptions of patched, by itself or its role with hedgehog may be found in Hooper and Scott, Cell 59, 751–765 (1989); Nakano et al., Nature, 341, 508–513 (1989) (both of which also describes the sequence for Drosophila patched) Simcox et al., Development 107, 715–722 (1989); Hidalgo and Ingham, Development, 110, 291–301 (1990); Phillips et al., Development, 110, 105–114 (1990); Sampedro and Guerrero, Nature 353, 187–190 (1991); Ingham et al., Nature 353, 184–187 (1991); and Taylor et al., Mechanisms of Development 42, 89–96 (1993). Discussions of the role of hedgehog include Riddle et al., Cell 75, 1401–1416 (1993); Echelard et al., Cell 75, 1417–1430 (1993); Krauss et al., Cell 75, 1431–1444 (1993); Tabata and Kornberg, Cell 76, 89–102 (1994); Heemskerk & DiNardo, Cell 76, 449–460 (1994); Relink et al., Cell 76, 761–775 (1994); and a short review article by Ingham, Current Biology 4, 347–350 (1994). The sequence for the Drosophila 5' non-coding region was reported to the GenBank, accession number M28418, referred to in Hooper and Scott (1989), supra. See also, Forbes, et al., Development 1993 Supplement 115–124.

SUMMARY OF THE INVENTION

Methods for isolating patched genes, particularly mammalian patched genes, including the mouse and human patched genes, as well as invertebrate patched genes and sequences, are provided. The methods include identification of patched genes from other species, as well as members of the same family of proteins. The subject genes provide methods for producing the patched protein, where the genes and proteins may be used as probes for research, diagnosis, binding of hedgehog protein for its isolation and purification, gene therapy, as well as other utilities.

BRIEF DESCRIPTION OF THE DRAWINGS

FIG. 1 is a graph having a restriction map of about 10kbp of the 5' region upstream from the initiation codon of Drosophila patched gene and bar graphs of constructs of truncated portions of the 5' region joined to β-galactosidase, where the constructs are introduced into fly cell lines for the production of embryos. The expression of β-gal in the embryos is indicated in the right-hand table during early and late development of the embryo. The greater the number of +'s, the more intense the staining.

DESCRIPTION OF THE SPECIFIC EMBODIMENTS

Methods are provided for identifying members of the patched (ptc) gene family from invertebrate and vertebrate, e.g. mammalian, species, as well as the entire cDNA sequence of the mouse and human patched gene. Also, sequences for invertebrate patched genes are provided. The patched gene encodes a transmembrane protein having a large number of transmembrane sequences.

In identifying the mouse and human patched genes, primers were employed to move through the evolutionary tree from the known Drosophila ptc sequence. Two primers are employed from the Drosophila sequence with appropriate restriction enzyme linkers to amplify portions of genomic DNA of a related invertebrate, such as mosquito. The sequences are selected from regions which are not likely to diverge over evolutionary time and are of low degeneracy. Conveniently, the regions are the N-terminal proximal sequence, generally within the first 1.5kb, usually within the first 1kb, of the coding portion of the cDNA, conveniently in the first hydrophilic loop of the protein. Employing the polymerase chain reaction (PCR) with the primers, a band can be obtained from mosquito genomic DNA. The band may then be amplified and used in turn as a probe. One may use this probe to probe a cDNA library from an organism in a different branch of the evolutionary tree, such as a butterfly. By screening the library and identifying sequences which hybridize to the probe, a portion of the butterfly patched gene may be obtained. One or more of the resulting clones may then be used to rescreen the library to obtain an extended sequence, up to and including the entire coding region, as well as the non-coding 5'- and 3'-sequences. As appropriate, one may sequence all or a portion of the resulting cDNA coding sequence.

One may then screen a genomic or cDNA library of a species higher in the evolutionary scale with appropriate probes from one or both of the prior sequences. Of particular interest is screening a genomic library, of a distantly related invertebrate, e.g. beetle, where one may use a combination of the sequences obtained from the previous two species, in this case, the Drosophila and the butterfly. By appropriate techniques, one may identify specific clones which bind to the probes, which may then be screened for cross hybridization with each of the probes individually. The resulting fragments may then be amplified, e.g. by subcloning.

By having all or parts of the 4 different patched genes, in the presently illustrated example, Drosophila (fly), mosquito, butterfly and beetle, one can now compare the patched genes for conserved sequences. Cells from an appropriate mammalian limb bud or other cells expressing patched, such as notochord, neural tube, gut, lung buds, or other tissue, particularly fetal tissue, may be employed for screening. Alternatively, adult tissue which produces patched may be employed for screening. Based on the consensus sequence available from the 4 other species, one can develop probes where at each site at least 2 of the sequences have the same nucleotide and where the site varies that each species has a unique nucleotide, inosine may be used, which binds to all 4 nucleotides.

Either PCR may be employed using primers or, if desired, a genomic library from an appropriate source may be probed. With PCR, one may use a cDNA library or use reverse transcriptase-PCR (RT-PCR), where mRNA is available from the tissue. Usually, where fetal tissue is employed, one will employ tissue from the first or second trimester, preferably the latter half of the first trimester or the second trimester, depending upon the particular host. The age and source of tissue will depend to a significant degree on the ability to surgically isolate the tissue based on its size, the level of expression of patched in the cells of the tissue, the accessibility of the tissue, the number of cells expressing patched and the like. The amount of tissue available should be large enough so as to provide for a sufficient amount of mRNA to be usefully transcribed and amplified. With mouse tissue, limb bud of from about 10 to 15 dpc (days post conception) may be employed.

In the primers, the complementary binding sequence will usually be at least 14 nucleotides, preferably at least about 17 nucleotides and usually not more than about 30 nucleotides. The primers may also include a restriction enzyme sequence for isolation and cloning. With RT-PCR, the mRNA may be enriched in accordance with known ways, reverse transcribed, followed by amplification with the appropriate primers. (Procedures employed for molecular cloning may be found in Molecular Cloning: A Laboratory Manual, Sambrook et al., eds., Cold Spring Harbor Laboratories, Cold Spring Harbor, N.Y., 1988). Particularly, the primers may conveniently come from the N-terminal proximal sequence or other conserved region, such as those sequences where at least five amino acids are conserved out of eight amino acids in three of the four sequences. This is illustrated by the sequences (SEQ ID NO: 11) IITPLDCFWEG, (SEQ ID NO: 12) LIVGG, and (SEQ ID NO: 13) PFFWEQY. Resulting PCR products of expected size are subcloned and may be sequenced if desired.

The cloned PCR fragment may then be used as a probe to screen a cDNA library of mammalian tissue cells expressing patched, where hybridizing clones may be isolated under appropriate conditions of stringency. Again, the CDNA library should come from tissue which expresses patched, which tissue will come within the limitations previously described. Clones which hybridize may be subcloned and rescreened. The hybridizing subclones may then be isolated and sequenced or may be further analyzed by employing RNA blots and in situ hybridizations in whole and sectioned embryos. Conveniently, a fragment of from about 0.5 to 1kbp of the N-terminal coding region may be employed for the Northern blot.

The mammalian gene may be sequenced and as described above, conserved regions identified and used as primers for investigating other species. The N-terminal proximal region, the C-terminal region or an intermediate region may be employed for the sequences, where the sequences will be selected having minimum degeneracy and the desired level of conservation over the probe sequence.

The DNA sequence encoding PTC may be cDNA or genomic DNA or fragment thereof, particularly complete exons from the genomic DNA, may be isolated as the sequence substantially free of wild-type sequence from the chromosome, may be a 50 kbp fragment or smaller fragment, may be joined to heterologous or foreign DNA, which may be a single nucleotide, oligonucleotide of up to 50 bp, which may be a restriction site or other identifying DNA for use as a primer, probe or the like, or a nucleic acid of greater than 50 bp, where the nucleic acid may be a portion of a cloning or expression vector, comprise the regulatory regions of an expression cassette, or the like. The DNA may be isolated, purified being substantially free of proteins and other nucleic acids, be in solution, or the like.

The subject gene may be employed for producing all or portions of the patched protein. The subject gene or fragment thereof, generally a fragment of at least 12 bp, usually at least 18 bp, may be introduced into an appropriate vector for extrachromosomal maintenance or for integration into the host. Fragments will usually be immediately joined at the 5' and/or 3' terminus to a nucleotide or sequence not found in the natural or wild-type gene, or joined to a label other than a nucleic acid sequence. For expression, an expression cassette may be employed, providing for a transcriptional and translational initiation region, which may be inducible or constitutive, the coding region under the transcriptional control of the transcriptional initiation region, and a transcriptional and translational termination region. Various transcriptional initiation regions may be employed which are functional in the expression host. The peptide may be expressed in prokaryotes or eukaryotes in accordance with conventional ways, depending upon the purpose for expression. For large production of the protein, a unicellular organism or cells of a higher organism, e.g. eukaryotes such as vertebrates, particularly mammals, may be used as the expression host, such as *E. coli, B, subtilis, S. cerevisiae,* and the like. In many situations, it may be desirable to express the patched gene in a mammalian host, whereby the patched gene will be transported to the cellular membrane for various studies. The protein has two parts which provide for a total of six transmembrane regions, with a total of six extracellular loops, three for each part. The character of the protein has similarity to a transporter protein. The protein has two conserved glycosylation signal triads.

The subject nucleic acid sequences may be modified for a number of purposes, particularly where they will be used intracellularly, for example, by being joined to a nucleic acid cleaving agent, e.g. a chelated metal ion, such as iron or chromium for cleavage of the gene; as an antisense sequence; or the like. Modifications may include replacing oxygen of the phosphate esters with sulfur or nitrogen, replacing the phosphate with phosphoramide, etc.

With the availability of the protein in large amounts by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to 100% pure. By pure is intended free of other proteins, as well as cellular debris.

The polypeptide may be used for the production of antibodies, where short fragments provide for antibodies specific for the particular polypeptide, whereas larger fragments or the entire gene allow for the production of antibodies over the surface of the polypeptide or protein, where the protein may be in its natural conformation.

Antibodies may be prepared in accordance with conventional ways, where the expressed polypeptide or protein may be used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen may be isolated, the splenocytes immortalized, and then screened for high affinity antibody binding. The immortalized cells, e.g. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutigenized by cloning in *E. coli,* and the heavy and light chains may be mixed to further enhance the affinity of the antibody. The antibodies may find use in diagnostic assays for detection of the presence of the PTC protein on the surface of cells or to inhibit the transduction of signal by the PTC protein ligand by competing for the binding site.

The mouse patched gene (SEQ ID NO:09) encodes a protein (SEQ ID NO:10) which has about 38% identical amino acids to fly PTC (SEQ ID NO:6) over about 1,200 amino acids. This amount of conservation is dispersed through much of the protein excepting the C-terminal region. The mouse protein also has a 50 amino acid insert relative to the fly protein. The human patched gene (SEQ ID NO:18) contains an open reading fram of about 1450 amino acids (SEQ ID NO:19) that is about 96% identical (98 % similar) to mouse ptc (SEQ ID NO:09). The human patched gene (SEQ ID NO:18), including coding and non-coding sequences, is about 89% identical to the mouse patched gene (SEQ ID NO:09).

The butterfly PTC homolog (SEQ ID NO:4) is 1,300 amino acids long and overall has a 50% amino acid identity (72% similarity) to fly PTC (SEQ ID NO:6). With the exception of a divergent C-terminus, this homology is evenly spread across the coding sequence. A 267bp exon from the beetle patched gene encodes an 89 amino acid protein fragment which was found to be 44 % and 51 % identical to the corresponding regions of fly and butterfly PTC respectively.

The mouse ptc message is about 8 kb long and the message is present in low levels as early as 7 dpc, the abundancy increasing by 11 and 15 dpc. Northern blot indicates a clear decrease in the amount of message at 17 dpc. In the adult, PTC RNA is present in high amounts in the brain and lung, as well as in moderate amounts in the kidney and liver. Weak signals are detected in heart, spleen, skeletal muscle and testes.

In mouse embryos, ptc mRNA is present at 7 dpc, using in situ hybridization. ptc is present at high levels along the neural axis of 8.5 dpc embryos. By 11.5 dpc, ptc can be detected in developing lung buds and gut, consistent with its Northern profile. In addition, the gene is present at high levels in the ventricular zone of the central nervous system as well as in the zona limitans of the prosencephalon. ptc is also strongly transcribed in the perichondrium condensing cartilage of 11.5 and 13.5 dpc limb buds, as well as in the ventral portion of the somites, a region which is prospective sclerotome and eventually forms bone in the vertebral column. PTC is present in a wide range of tissues from endodermal, mesodermal, as well as ectodermal origin, evidencing the fundamental role in many aspects of embryonic development, including the condensation of cartilage, the patterning of limbs, the differentiation of lung tissue, and the generation of neurons.

The patched nucleic acid may be used for isolating the gene from various mammalian sources of interest, particularly primate, more particularly human, or from domestic animals, both pet and farm, e.g. lagomorpha, rodentiae, porcine, bovine, feline, canine, ovine, equine, etc. By using probes, particularly labeled probes of DNA sequences, of the patched gene, one may be able to isolate mRNA or genomic DNA, which may be then used for identifying mutations, particularly associated with genetic diseases, such as spina bifida, limb defects, lung defects, problems with tooth development, liver and kidney development, peripheral nervous system development, and other sites where a patched gene is involved in regulation. The subject probes can also be used for identifying the level of expression in cells associated with the testis to determine the relationship with the level of expression and sperm production.

The gene or fragments thereof may be used as probes for identifying the 5' non-coding region comprising the transcriptional initiation region, particularly the enhancer regulating the transcription of patched. By probing a genomic library, particularly with a probe comprising the 5' coding region, one can obtain fragments comprising the 5' non-coding region. If necessary, one may walk the fragment to obtain further 5' sequence to ensure that one has at least a functional portion of the enhancer. It is found that the enhancer is proximal to the 5' coding region, a portion being in the transcribed sequence and downstream from the promoter sequences. The transcriptional initiation region may be used for many purposes, studying embryonic development, providing for regulated expression of patched protein or other protein of interest during embryonic development or thereafter, and in gene therapy.

The gene may also be used for gene therapy, by transfection of the normal gene into embryonic stem cells or into mature cells. A wide variety of viral vectors can be employed for transfection and stable integration of the gene into the genome of the cells. Alternatively, micro-injection may be employed, fusion, or the like for introduction of genes into a suitable host cell. See, for example, Dhawan et al., Science 254, 1509–1512 (1991) and Smith et al., Molecular and Cellular Biology (1990) 3268–3271.

By providing for the production of large amounts of PTC protein, one can use the protein for identifying ligands which bind to the PTC protein. Particularly, one may produce the protein in cells and employ the polysomes in columns for isolating ligands for the PTC protein. One may incorporate the PTC protein into liposomes by combining the protein with appropriate lipid surfactants, e.g. phospholipids, cholesterol, etc., and sonicate the mixture of the PTC protein and the surfactants in an aqueous medium. With one or more established ligands, e.g. hedgehog, one may use the PTC protein to screen for antagonists which inhibit the binding of the ligand. In this way, drugs may be identified which can prevent the transduction of signals by the PTC protein in normal or abnormal cells.

The PTC protein, particularly binding fragments thereof, the gene encoding the protein, or fragments thereof, particularly fragments of at least about 18 nucleotides, frequently of at least about 30 nucleotides and up to the entire gene, more particularly sequences associated with the hydrophilic loops, may be employed in a wide variety of assays. In these situations, the particular molecules will normally be joined to another molecule, serving as a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which provides for detection, in accordance with known procedures. The assays may be used for detecting the presence of molecules which bind to the patched gene or PTC protein, in isolating molecules which bind to the patched gene, for measuring the amount of patched, either as the protein or the message, for identifying molecules which may serve as agonists or antagonists, or the like.

Various formats may be used in the assays. For example, mammalian or invertebrate cells may be designed where the cells respond when an agonist binds to PTC in the membrane of the cell. An expression cassette may be introduced into the cell, where the transcriptional initiation region of patched is joined to a marker gene, such as β-galactosidase, for which a substrate forming a blue dye is available. A 1.5kb fragment that responds to PTC signaling has been identified and shown to regulate expression of a heterologous gene during embryonic development. When an agonist binds to the PTC protein, the cell will turn blue. By employing a competition between an agonist and a compound of interest, absence of blue color formation will indicate the presence of an antagonist. These assays are well known in the literature. Instead of cells, one may use the protein in a membrane environment and determine binding affinities of compounds. The PTC may be bound to a surface and a labeled ligand for PTC employed. A number of labels have been indicated previously. The candidate compound is added with the labeled ligand in an appropriate buffered medium to the surface bound PTC. After an incubation to ensure that binding has occurred, the surface may be washed free of any non-specifically bound components of the assay medium, particularly any non-specifically bound labeled ligand, and any label bound to the surface determined. Where the label is an enzyme, substrate producing a detectable product may be used. The label may be detected and measured. By using standards, the binding affinity of the candidate compound may be determined.

The availability of the gene and the protein allows for investigation of the development of the fetus and the role patched and other molecules play in such development. By employing antisense sequences of the patched gene, where the sequences may be introduced in cells in culture, or a vector providing for transcription of the antisense of the patched gene introduced into the cells, one can investigate the role the PTC protein plays in the cellular development. By providing for the PTC protein or fragment thereof in a soluble form which can compete with the normal cellular PTC protein for ligand, one can inhibit the binding of ligands to the cellular PTC protein to see the effect of variation in concentration of ligands for the PTC protein on the cellular development of the host. Antibodies against PTC can also be used to block function, since PTC is exposed on the cell surface.

The subject gene may also be used for preparing transgenic laboratory animals, which may serve to investigate embryonic development and the role the PTC protein plays in such development. By providing for variation in the expression of the PTC protein, employing different transcriptional initiation regions which may be constitutive or inducible, one can determine the developmental effect of the differences in PTC protein levels. Alternatively, one can use the DNA to knock out the PTC protein in embryonic stem cells, so as to produce hosts with only a single functional patched gene or where the host lacks a functional patched gene. By employing homologous recombination, one can introduce a patched gene, which is differentially regulated, for example, is expressed to the development of the fetus, but not in the adult. One may also provide for expression of the patched gene in cells or tissues where it is not normally expressed or at abnormal times of development. One may provide for mis-expression or failure of expression in certain tissue to mimic a human disease. Thus, mouse models of spina bifida or abnormal motor neuron differentiation in the developing spinal cord are made available. In addition, by providing expression of PTC protein in cells in which it is otherwise not normally produced, one can induce changes in cell behavior upon binding of ligand to the PTC protein.

Areas of investigation may include the development of cancer treatments. The wingless gene, whose transcription is regulated in flies by PTC, is closely related to a mammalian oncogene, Wnt-1, a key factor in many cases of mouse breast cancer. Other Wnt family members, which are secreted signaling proteins, are implicated in many aspects of development. In flies, the signaling factor decapentaplegic, a member of the TGF-beta family of signaling proteins, known to affect growth and development in mammals, is also controlled by PTC. Since members of both the TGF-beta and Wnt families are expressed in mice in places close to overlapping with patched, the common regulation provides an opportunity in treating cancer. Also, for repair and regeneration, proliferation competent cells making PTC protein can find use to promote regeneration and healing for damaged tissue, which tissue may be regenerated by transfecting cells of damaged tissue with the ptc gene and its normal transcription initiation region or a modified transcription initiation region. For example, PTC may be useful to stimulate growth of new teeth by engineering cells of the gums or other tissues where PTC protein was during an earlier developmental stage or is expressed.

Since Northern blot analysis indicates that ptc is present at high levels in adult lung tissue, the regulation of ptc expression or binding to its natural ligand may serve to inhibit proliferation of cancerous lung cells. The availability of the gene encoding PTC and the expression of the gene allows for the development of agonists and antagonists. In addition, PTC is central to the ability of neurons to differentiate early in development. The availability of the gene allows for the introduction of PTC into host diseased tissue, stimulating the fetal program of division and/or differentiation. This could be done in conjunction with other genes which provide for the ligands which regulate PTC activity or by providing for agonists other than the natural ligand.

The availability of the coding region for various ptc genes from various species, allows for the isolation of the 5' non-coding region comprising the promoter and enhancer associated with the ptc genes, so as to provide transcriptional and post- transcriptional regulation of the ptc gene or other genes, which allow for regulation of genes in relation to the regulation of the ptc gene. Since the ptc gene is autoregulated, activation of the ptc gene will result in activation of transcription of a gene under the transcriptional control of the transcriptional initiation region of the ptc gene. The transcriptional initiation region may be obtained from any host species and introduced into a heterologous host species, where such initiation region is functional to the desired degree in the foreign host. For example, a fragment of from about 1.5 kb upstream from the initiation codon, up to about 10kb, preferably up to about 5 kb may be used to provide for transcriptional initiation regulated by the PTC protein, particularly the Drosophila 5' -non-coding region (GenBank accession no. M28418).

The following examples are offered by illustration not by way of limitation.

EXPERIMENTAL

Methods and Materials

I. PCR on Mosquito (Anopheles gambiae) Genomic DNA

PCR primers were based on amino acid stretches of fly PTC that were not likely to diverge over evolutionary time and were of low degeneracy. Two such primers (P2R1 (SEQ ID NO:14): GGACGAATTCAARGTNCAYCARYTNTGG, P4R1: (SEQ ID NO:15) GGACGAATTCCYTCCCARAARCANTC, (the underlined sequences are Eco RI linkers) amplified an appropriately sized band from mosquito genomic DNA using the PCR. The program conditions were as follows:

94° C. 4 min.; 72° C. Add Taq;
[49° C. 30 sec.; 72° C. 90 sec.; 94° C. 15 sec] 3 times
[94° C. 15 sec.; 50° C. 30 sec.; 72° C. 90 sec] 35 times
72° C. 10 min; 4° C. hold This band was subcloned into the EcoRV site of pBluescript II and sequenced using the USB Sequence kit.

II. Screen of a Butterfly cDNA Library with Mosquito PCR Product

Using the mosquito PCR product (SEQ ID NO:7) as a probe, a 3 day embryonic *Precis coenia* λgt10 cDNA library (generously provided by Sean Carroll) was screened. Filters were hybridized at 65° C. overnight in a solution containing 5×SSC, 10% dextran sulfate, 5× Denhardt's, 200 μg/ml sonicated salmon sperm DNA, and 0.5% SDS. Filters were washed in 0.1×SSC, 0.1% SDS at room temperature several times to remove nonspecific hybridization. Of the 100,000 plaques initially screened, 2 overlapping clones, L1 and L2, were isolated, which corresponded to the N terminus of butterfly PTC. Using L2 as a probe, the library filters were rescreened and 3 additional clones (L5, L7, L8) were isolated which encompassed the remainder of the ptc coding sequence. The full length sequence of butterfly ptc (SEQ ID NO:3) was determined by ABI automated sequencing.

III. Screen of a Tribolium (beetle) Genomic Library with Mosquito PCR Product and 900 bp Fragment from the Butterfly Clone A λgem 11 genomic library from *Tribolium casteneum* (gift of Rob Dennell) was probed with a mixture of the mosquito PCR (SEQ ID NO:7) product and BstXI/EcoRI fragment of L2. Filters were hybridized at 55° C. overnight and washed as above. Of the 75,000 plaques screened, 14 clones were identified and the SacI fragment of T8 (SEQ ID NO:1), which crosshybridized with the mosquito and butterfly probes, was subcloned into pBluescript.

IV. PCR on Mouse cDNA Using Degenerate Primers Derived from Regions Conserved in the Four Insect Homologues Two degenerate PCR primers (P4REV: (SEQ ID NO: 16) GGACGAATTCYTNGANTGYTTYTGGGA; P22: (SEQ ID NO:17) CATACCAGCCAAGCTTGTCIGGCCARTGCAT) were designed based on a comparison of PTC amino acid sequences from fly (*Drosophila melanogaster*) (SEQ ID NO:6), mosquito (*Anopheles gambiae*)(SEQ ID NO:8), butterfly (Precis *coenia*)(SEQ ID NO:4), and beetle (*Tribolium casteneum*)(SEQ ID NO:2). I represents inosine, which can form base pairs with all four nucleotides. P22 was used to reverse transcribe RNA from 12.5 dpc mouse limb bud (gift from David Kingsley) for 90 min at 37° C. PCR using P4REV(SEQ ID NO:17) and P22(SEQ ID NO:18) was then performed on 1 μl of the resultant cDNA under the following conditions:

94° C. 4 min.; 72° C. Add Taq;
[94° C. 15 sec.; 50° C. 30 sec.; 72° C. 90 sec.] 35 times
72° C. 10 min.; 4° C. hold PCR products of the expected size were subcloned into the TA vector (Invitrogen) and sequenced with the Sequenase Version 2.0 DNA Sequencing Kit (U.S.B.).

Using the cloned mouse PCR fragment as a probe, 300,000 plaques of a mouse 8.5 dpc λgt10 cDNA library (a gift from Brigid Hogan) were screened at 65° C. as above and washed in 2x SSC, 0.1% SDS at room temperature. 7 clones were isolated, and three (M2 M4, and M8) were subcloned into pBluescript II. 200,000 plaques of this library were rescreened using first, a 1.1 kb EcoRI fragment from M2 to identify 6 clones (M9–M16) and secondly a mixed probe containing the most N terminal (XhoI fragment from M2) and most C terminal sequences (BamHI/BglII fragment from M9) to isolate 5 clones (M17–M21). M9, M10, M14, and M17–21 were subcloned into the EcoRI site of pBluescript II (Strategene).

V. RNA Blots and in situ Hybridizations in Whole and Sectioned Mouse Embryos Northerns:

A mouse embryonic Northern blot and an adult multiple tissue Northern blot (obtained from Clontech) were probed with a 900 bp EcoRI fragment from an N terminal coding region of mouse ptc. Hybridization was performed at 65° C. in 5x SSPE, 10x Denhardt's, 100 µg/ml sonicated salmon sperm DNA, and 2% SDS. After several short room temperature washes in 2x SSC, 0.05% SDS, the blots were washed at high stringency in 0.1x SSC, 0.1% SDS at 50C.

In situ hybridization of sections:

7.75, 8.5, 11.5, and 13.5 dpc mouse embryos were dissected in PBS and frozen in Tissue-Tek medium at −80° C. 12–16 µm frozen sections were cut, collected onto Vecta-Bond (Vector Laboratories) coated slides, and dried for 30–60 minutes at room temperature. After a 10 minute fixation in 4% paraformaldehyde in PBS, the slides were washed 3 times for 3 minutes in PBS, acetylated for 10 minutes in 0.25% acetic anhydride in triethanolamine, and washed three more times for 5 minutes in PBS. Prehybridization (50% formamide, 5x SSC, 250 µg/ml yeast tRNA, 500 µg/ml sonicated salmon sperm DNA, and 5x Denhardt's) was carried out for 6 hours at room temperature in 50% formamide/5x SSC humidified chambers. The probe, which consisted of 1 kb from the N-terminus of ptc, was added at a concentration of 200–1000 ng/ml into the same solution used for prehybridization, and then denatured for five minutes at 80° C. Approximately 75 µl of probe were added to each slide and covered with Parafilm. The slides were incubated overnight at 65° C. in the same humidified chamber used previously. The following day, the probe was washed successively in 5x SSC (5 minutes, 65° C.), 0.2x SSC (1 hour, 65° C.), and 0.2x SSC (10 minutes, room temperature). After five minutes in buffer B1 (0.1 M maleic acid, 0.15 M NaCl, pH 7.5), the slides were blocked for 1 hour at room temperature in 1 % blocking reagent (Boerhinger-Mannheim) in buffer B1, and then incubated for 4 hours in buffer B1 containing the DIG-AP conjugated antibody (Boerhinger-Mannheim) at a 1:5000 dilution. Excess antibody was removed during two 15 minute washes in buffer B1, followed by five minutes in buffer B3 (100 mM Tris, 100mM NaCl, 5mM MgCl$_2$, pH 9.5). The antibody was detected by adding an alkaline phosphatase substrate (350 µl 75 mg/ml X-phosphate in DMF, 450 µl 50 mg/ml NBT in 70% DMF in 100 mls of buffer B3) and allowing the reaction to proceed over-night in the dark. After a brief rinse in 10 mM Tris, 1mM EDTA, pH 8.0, the slides were mounted with Aquamount (Lerner Laboratories).

VI. Drosophila 5-transcriptional initiation region µ-gal constructs.

A series of constructs were designed that link different regions of the ptc promoter from Drosophila to a LacZ reporter gene in order to study the cis regulation of the ptc expression pattern. See FIG. 1. A 10.8kb BamHI/BspM 1 fragment comprising the 5'-non-coding region of the mRNA at its 3'-terminus was obtained and truncated by restriction enzyme digestion as shown in FIG. 1. These expression cassettes were introduced into Drosophila lines using a P-element vector (Thummel et al., Gene 74, 445–456 (1988), which were injected into embryos, providing flies which could be grown to produce embryos. (See Spradling and Rubin, Science (1982) 218, 341–347 for a description of the procedure.) The vector used a pUC8 background into which was introduced the white gene to provide for yellow eyes, portions of the P-element for integration, and the constructs were inserted into a polylinker upstream from the LacZ gene. The resulting embryos were stained using antibodies to LacZ protein conjugated to HRP and the embryos developed with OPD dye to identify the expression of the LacZ gene. The staining pattern is described in FIG. 1, indicating whether there was staining during the early and late development of the embryo.

VII. Isolation of a Mouse ptc Gene

Homologues of fly PTC (SEQ ID NO:6) were isolated from three insects: mosquito, butterfly and beetle, using either PCR or low stringency library screens. PCR primers to six amino acid stretches of PTC of low mutatability and degeneracy were designed. One primer pair, P2 and P4, amplified an homologous fragment of ptc from mosquito genomic DNA that corresponded to the first hydrophilic loop of the protein. The 345bp PCR product (SEQ ID NO:7) was subcloned and sequenced and when aligned to fly PTC, showed 67% amino acid identity.

The cloned mosquito fragment was used to screen a butterfly λGT 10 cDNA library. Of 100,000 plaques screened, five overlapping clones were isolated and used to obtain the full length coding sequence. The butterfly PTC homologue (SEQ ID NO:4) is 1,311 amino acids long and overall has 50% amino acid identity (72% similarity) to fly PTC. With the exception of a divergent C-terminus, this homology is evenly spread across the coding sequence. The mosquito PCR clone (SEQ ID NO:7) and a corresponding fragment of butterfly cDNA were used to screen a beetle λgem11 genomic library. Of the plaques screened, 14 clones were identified. A fragment of one clone (T8), which hybridized with the original probes, was subcloned and sequenced. This 3kb piece contains an 89 amino acid exon (SEQ ID NO:2) which is 44% and 51% identical to the corresponding regions of fly and butterfly PTC respectively.

Using an alignment of the four insect homologues in the first hydrophilic loop of the PTC, two PCR primers were designed to a five and six amino acid stretch which were identical and of low degeneracy. These primers were used to isolate the mouse homologue using RT-PCR on embryonic limb bud RNA. An appropriately sized band was amplified and upon cloning and sequencing, it was found to encode a protein 65% identical to fly PTC. Using the cloned PCR product and subsequently, fragments of mouse ptc cDNA, a mouse embryonic AcDNA library was screened. From about 300,000 plaques, 17 clones were identified and of these, 7 form overlapping cDNA's which comprise most of the protein-coding sequence (SEQ ID NO:9).

VIIa. Developmental and Tissue Distribution of Mouse PTC RNA

In both the embryonic and adult Northern blots, the ptc probe detects a single 8kb message. Further exposure does not reveal any additional minor bands. Developmentally, ptc mRNA is present in low levels as early as 7 dpc and becomes quite abundant by 11 and 15 dpc. While the gene is still present at 17 dpc, the Northern blot indicates a clear decrease in the amount of message at this stage. In the adult, ptc RNA is present in high amounts in the brain and lung, as well as in moderate amounts in the kidney and liver. Weak signals are detected in heart, spleen, skeletal muscle, and testes.

VIIB. In situ Hybridization of Mouse PTC in Whole and Section Embryos

Northern analysis indicates that ptc mRNA is present at 7 dpc, while there is no detectable signal in sections from 7.75 dpc embryos. This discrepancy is explained by the low level of transcription. In contrast, ptc is present at high levels along the neural axis of 8.5 dpc embryos. By 11.5 dpc, ptc can be detected in the developing lung buds and gut, consistent with its adult Northern profile. In addition, the gene is present at high levels in the ventricular zone of the central nervous system, as well as in the zona limitans of the prosencephalon. ptc is also strongly transcribed in the condensing cartilage of 11.5 and 13.5 dpc limb buds, as well as in the ventral portion of the somites, a region which is prospective sclerotome and eventually forms bone in the vertebral column. ptc is present in a wide range of tissues from endodermal, mesodermal and ectodermal origin supporting its fundamental role in embryonic development.

VIII. Isolation of the Human ptc Gene

To isolate human ptc (hptc), $2\times10^5$ plaques from a human lung cDNA library (HL3022a, Clonetech) were screened with a 1kbp mouse ptc fragment, M2-2. Filters were hybridized overnight at reduced stringency (60° C. in 5× SSC, 10% dextran sulfate, 5× Denhardt's, 0.2 mg/ml sonicated salmon sperm DNA, and 0.5% SDS). Two positive plaques (H1 and H2) were isolated, the inserts cloned into pBluescript, and upon sequencing, both contained sequence highly similar to the mouse ptc homolog. To isolate the 5' end, an additional $6\times10^5$ plaques were screened in duplicate with M2–3 EcoRI I and M2–3 XhoI I (containing 5' untranslated sequence of mouse ptc) probes. Ten plaques were purified and of these, 6 inserts were subcloned into pBluescript. To obtain the full coding sequence, H2 was fully and H14, H20, and H21 were partially sequenced. The 5.1kbp of human ptc sequence (SEQ ID NO:18) contains an open reading frame of 1447 amino acids (SEQ ID NO:19) that is 96% identical and 98% similar to mouse ptc. The 5' and 3' untranslated sequences of human ptc (SEQ ID NO:18) are also highly similar to mouse ptc (SEQ ID NO:09) suggesting conserved regulatory sequence.

IX. Comparison of Mouse, Human, Fly and Butterfly Sequences

The deduced mouse PTC protein sequence (SEQ ID NO:10) has about 38% identical amino acids to fly PTC over about 1,200 amino acids. This amount of conservation is dispersed through much of the protein excepting the C-terminal region. The mouse protein also has a 50 amino acid insert relative to the fly protein. Based on the sequence conservation of PTC and the functional conservation of hedgehog between fly and mouse, one concludes that ptc functions similarly in the two organisms. A comparison of the amino acid sequences of mouse (mptc) (SEQ ID NO:10), human (hptc) (SEQ ID NO:19), butterfly (bptc)(SEQ ID NO:4) and drosophila (ptc) (SEQ ID NO:6) is shown in Table 1.

TABLE 1 alignment of human, mouse, fly, and butterfly PTC homologs

```
HPTC   MAS AGNAALP QDR - - GGGGS GCI GAP GRP AGGGRRRRT GGL RRAAAP DR DYL HRP S YCDA
MPTC   MAS AGNAA - - - - - - - - - - - - - - - GAL GR QAGGGRRRRT GGP HRA - AP DR DYL HRP P YCDA
PTC    M - - - - - DRDSLPRVPDTHGD - - VVDE - - - - - - - - - KLFSDL - - - - - - - - - YI - RTS WVDA
BPTC   MVAPDSEAPSNPRI TAAHESPCATEA - - - - - - - - - RHSADL - - - - - - - - - YI - RTS WVDA
              *                           .   . .                         *. *   *   * *

HPTC   AF ALE QI SKGKAT GRKAP LWL RAKF QRLLF KLGCYI QKNCGKF LVVGLLI FGAFAVGLKA
MPTC   AF ALE QI SKGKAT GRKAP LWL RAKF QRLLF KLGCYI QKNCGKF LVVGLLI FGAFAVGLKA
PTC    QVALDQI DKGKARGSRTAI YLRS VFQS HLETLGSS VQKHAGKVLF VAI LVLSTFCVGLKS
BPTC   ALALSELEKGNI EGGRTSLWI RAWLQEQLFI LGCFLQGDAGKVLF VAI LVLSTFCVGLKS
       * *    . .    * *.   *   . . . . . *.   . *     *   * *   . *   . * *   * *. . . *  . . . . *  * * * *.

HPTC   ANLETNVEELWVEVGGRVSRELNYTRQKI GEEAMF NP QLMI QTP KEEGANVLTTEALLQH
MPTC   ANLETNVEELWVEVGGRVSRELNYTRQKI GEEAMF NP QLMI QTP KEEGANVLTTEALLQH
PTC    AQI HS KVHQLWI QEGGRLEAELAYTQKTI GEDES ATHQLLI QTTHDP NAS VLHPQALLAH
BPTC   AQI HTRVDQLWVQEGGRLEAELKYTAQALGEADSSTHQLVI QTAKDPDVSLLHPGALLEH
       * .   .   .   * .   * *. *   . * * *.   . * * . * *   . *    * * .  * *. * * *   .  .   . *   * * *   *

HPTC   LDS AL QAS RVHVYMYNR QWKLEHLCYKS GELI TET - GYMDQI I EYLYP CLI I TP LDCF WE
MPTC   LDS AL QAS RVHVYMYNR QWKLEHLCYKS GELI TET - GYMDQI I EYLYP CLI I TP LDCF WE
PTC    LE VLVKATAVKVHL YDTE WGLRDMCNMP STP SFEGI YYI EQI LRHLI P CSI I TP LDCF WE
BPTC   LKVVHAATRVTVHMYDI EWRLKDLCYSPSI PDFEGYHHI ESI I DNVI P CAI I TP LDCF WE
       *         *.   *     *         . . *   . .   *     . .         *       . . * .       .   * *   * * * * * * * * * *

HPTC   GAKLQSGTAYLLGKPPLR - - - - WTNFDPLEFLEELK - - - - - - KI NYQVDS WEEMLNKAE V
MPTC   GAKLQSGTAYLLGKPPLR - - - - WTNFDPLEFLEELK - - - - - - KI NYQVDS WEEMLNKAE V
```

TABLE 1-continued alignment of human, mouse, fly, and butterfly PTC homologs

```
PTC    G S Q L L - G P E S A V V I P G L N Q R L L W T T L N P A S V M Q Y M K Q K M S E E K I S F D F E T V E Q Y M K R A A I
BPTC   G S K L L - G P D Y P I Y V P H L K H K L Q W T H L N P L E V V E E V K - K L - - - K F Q F P L S T I E A Y M K R A G I
       *  .  .  *     *           .  *    .  *  *      .  .  *           .  .  .  *           *  .        .        *     .  .  .  *  .

HPTC   G H G Y M D R P C L N P A D P D C P A T A P N K N S T K P L D M A L V L N G G C H G L S R K Y M H W Q E E L I V G G T V
MPTC   G H G Y M D R P C L N P A D P D C P A T A P N K N S T K P L D V A L V L N G G C Q G L S R K Y M H W Q E E L I V G G T V
PTC    G S G Y M E K P C L N P L N P N C P D T A P N K N S T Q P P D V G A I L S G G C Y G Y A A K H M H W P E E L I V G G R K
BPTC   T S A Y M K K P C L D P T D P H C P A T A P N K K S G H I P D V A A E L S H G C Y G F A A A T M H W P E Q L I V G G A T
       .  *  *  .  *  *  *  .  *  .  *  .  *  *  *  *  *  *  .        *  .  .     *  .     *  *  .     *  *  *  *  *  .  *  .  *  *  *  *  *

HPTC   K N S T G K L V S A H A L Q T M F Q L M T P K Q M Y E H F K G Y E Y V S H I N W N E D K A A A I L E A W Q R T Y V E V V
MPTC   K N A T G K L V S A H A L Q T M F Q L M T P K Q M Y E H F R G Y D Y V S H I N W N E D R A A A I L E A W Q R T Y V E V V
PTC    R N R S G H L R K A Q A L Q S V V Q L M T E K E M Y D Q W Q D N Y K V H H L G W T Q E K A A E V L N A W Q R N F S R E V
BPTC   R N S T A A L R S A R A L Q T V V Q L M G E R E M Y E Y W A D H Y K V H Q I G W N Q E K A A A V L D A W Q R K F A A E V
       .  *  .  .     .  *     .  *     *  .  *  *  *     .  .  .  *        .     *  *  .              .  .     *     .  *  *  *  *  .           *

HPYC   H Q S V A Q N S T Q K - - - - V L S F T T T T L D D I L K S F S D V S V I R V A S G Y L L M L A Y A C L T M L R W - D C
MPTC   H Q S V A P N S T Q K - - - - V L S F T T T T L D D I L K S F S D V S V I R V A S G Y L L M L A Y A C L T M L R W - D C
PTC    E Q L L R K Q S R I A T N Y D I Y V F S S A A L D D I L A K F S H P S A L S I V I G V A V T V L Y A F C T L L R W R D P
BPTC   R K I - T T S G S V S S A Y S F Y P F S T S T L N D I L G K F S E V S L K N I I L G Y M F M L I Y V A V T L I Q W R D P
                                     *  .  .  .  .     *  *  *           *  *           .  .     .     .                 *     *  .        *

HPTC   S K S Q G A V G L A G V L L V A L S V A A G L G L C S L I G I S F N A A T T Q V L P F L A L G V G V D D V F L L A H A F
MPTC   S K S Q G A V G L A G V L L V A L S V A A G L G L C S L I G I S F N A A T T Q V L P F L A L G V G V D D V F L L A H A F
PTC    V R G Q S S V G V A G V L L M C F S T A A G L G L S A L L G I V F N A A S T Q V V P F L A L G L G V D H I F M L T A A Y
BPTC   I R S Q A G V G I A G V L L L S I T V A A G L G F C A L L G I P F N A S S T Q I V P F L A L G L G V Q D M F L L T H T Y
       .  .  .     *  .  *  .  *  *  *  *  *  *     .           *  *  *  *  *  *     .  *  *  *     *  *  .  .  *  .  .  *  *  *  *  *  .  .     .     .     .  .

HPTC   S E T G Q N K R I P F E D R T G E C L K R T G A S V A L T S I S N V T A F F M A A L I P I P A L R A F S L Q A A V V V V
MPTC   S E T G Q N K R I P F E D R T G E C L K R T G A S V A L T S I S N V T A F F M A A L I P I P A L R A F S L Q A A V V V V
PTC    A E S N - - - - - - R R E Q T K L I L K K V G P S I L F S A C S T A G S F F A A A F I P V P A L K V F C L Q A A I V M C
BPTC   V E Q A G D - - V P R E E R T G L V L K K S G L S V L L A S L C N V M A F L A A A L L P I P A F R V F C L Q A A I L L L
           *                 .  .     *        *  *     .        .     .  .  .                 .  *     *  *     .  .  *  .     *  *  *  *     .  .  .

HPTC   F N F A M V L L I F P A I L S M D L Y R R E D R R L D I F C C F T S P C V S R V I Q V E P Q A Y T D T H D N T R Y S P P
MPTC   F N F A M V L L I F P A I L S M D L Y R R E D R R L D I F C C F T S P C V S R V I Q V E P Q A Y T E P H S N T R Y S P P
PTC    S N L A A A L L V F P A M I S L D L R R R T A G R A D I F C C C F - P V W K E Q P K V A P P V L P L N N N N G R - - - -
BPTC   F N L G S I L L V F P A M I S L D L R R R S A A R A D L L C C L M - P - - - E S P - - - - - - L P K K K I P E R - - - -
         *  .  .     .  .     *  *  .  *  *  *  .  .  *  *     *  *     *  *              *  *  .  *  *           *                          *

HPTC   P P Y S S H S F A H E T Q I T M Q S T V Q L R T E Y D P H T H V Y Y T T A E P R S E I S V Q P V T V T Q D T   L S C Q S P
MPTC   P P Y T S H S F A H E T H I T M Q S T V Q L R T E Y D P H T H V Y Y T T A E P R S E I S V Q P V T V T Q D N L S C Q S P
PTC    - - - - - - - - - - - - - - - - - - - - - - - - - - - - G A R H P K S C N N N R V P L P A Q N P L L E Q R A
BPTC   - - - - - - - - - - - - - - - - - - - - - - - - - - - - - - A K T R K N D K T H R I D - T T R Q P L D P D V S
                                                                     .        .  .                          .  .  .        *        .  .

HPTC   E S T S S T R D L L S Q F S D S S L H C L E P P C T K W T L S S F A E K H Y A P F L L K P K A K V V V I F L F L G L L G
MPTC   E S T S S T R D L L S Q F S D S S L H C L E P P C T K W T L S S F A E K H Y A P F L L K P K A K V V V I L L F L G L L G
PTC    D I P G S S - - - - - - - - - - - H S L A S F - - - - S L A T F A F Q H Y T P F L M R S W V K F L T V M G F L A A L I
HTPC   E N V T K T - - - - - - - - - - - C C L - S V - - - - S L T K W A K N Q Y A P F I M R P A V K V T S M L A L I A V I L
          .                                          *              .     *        *           *  .  *  *  *                 *

HPTC   V S L Y G T T R V R D G L D L T D I V P R E T R E Y D F I A A Q F K Y F S F Y N M Y I V T Q K A - D Y P N I Q H L L Y D
MPTC   V S L Y G T T R V R D G L D L T D I V P R E T R E Y D F I A A Q F K Y F S F Y N M Y I V T Q K A - D Y P N I Q H L L Y D
PTC    S S L Y A S T R L Q D G L D I I D L V P K D S N E H K F L D A Q T R L F G F Y S M Y A V T Q G N F E Y P T Q Q Q L L R D
```

TABLE 1-continued alignment of human, mouse, fly, and butterfly PTC homologs

```
BPTC   T S V W G A T K V K D G L D L T D I V P E N T D E H E F L S R Q E K Y F G F Y N M Y A V T Q G N F E Y P T N Q K L L Y E
         *   .   .  *   .  . * * * *   .  *   *  *     .  *     .     *  * *   * *   * * *     .   * *     .   *   * *   .

HPTC   L H R S F S N V K Y V M L E E N K Q L P K M W L H Y F R D W L Q G L Q D A F D S D W E T G K I M P N N - Y K N G S D D G
MPTC   L H K S F S N V K Y V M L E E N K Q L P Q M W L H Y F R D W L Q G L Q D A F D S D W E T G R I M P N N - Y K N G S D D G
PTC    Y H D S F V R V P H V I K N D N G G L P D F W L L L F S E W L G N L Q K I F D E E Y R D G R L T K E C W F P N A S S D A
BPTC   Y H D Q F V R I P N I I K N D N G G L T K F W L S L F R D W L L D L Q V A F D K E V A S G C I T Q E Y W C K N A S D E G
         *     *      .  .  .  . *     *   *     * *     . *     *   *     * *   . *      *      *     *   . *  *     .  .

HPTC   V L A Y K L L V Q T G S R D K P I D I S Q L T K - Q R L V D A D G I I N P S A F Y I Y L T A W V S N D P V A Y A A S Q A
MPTC   V L A Y K L L V Q T G S R D K P I D I S Q L T K - Q R L V D A D G I I N P S A F Y I Y L T A W V S N D P V A Y A A S Q A
PTC    I L A Y K L I V Q T G H V D N P V D K E L V L T - N R L V N S D G I I N Q R A F Y N Y L S A W A T N D V F A Y G A S Q G
BPTC   I L A Y K L M V Q T G H V D N P I D K S L I T A G H R L V D K D G I I N P K A F Y N Y L S A W A T N D A L A Y G A S Q G
       . * * * * .  * * * *     . * .  *      .       . * * .     * * * *   .   . * *   .  * *       * .  . *   . * * * .

HPTC   N I R P H R P E W V H D K A D Y M P E T R L R I P A A E P I E Y A Q F P F Y L N G L R D T S D F V E A I E K V R T I C S
MPTC   N I R P H R P E W V H D K A D Y M P E T R L R I P A A E P I E Y A Q F P F Y L N G L R D T S D F V E A I E K V R V I C N
PTC    K L Y P E P R Q Y F H Q P N E Y - - - - D L K I P K S L P L V Y A Q M P F Y L H G L T D T S Q I K T L I G H I R D L S V
BPTC   N L K P Q P Q R W I H S P E D V - - - - H L E I K K S S P L I Y T Q L P F Y L S G L S D T D S I K T L I R S V R D L C L
       .  .  *        .                       *     *    *    . .    *   * * * *   * *  . *  .      .  *   .        .

HPTC   N Y T S L G L S S Y P N G T P F L F W E Q Y I G L R H W L L L F I S V V L A C T F L V C A V F L L N P W T A G I I V M V
MPTC   N Y T S L G L S S Y P N G Y P F L F W E Q Y I S L R H W L L L S I S V V L A C T F L V C A V F L L N P W T A G I I V M V
PTC    K Y E G F G L P N Y P S G I P F I F W E Q Y M T L R S S L A M I L A C V L L A A L V L V S L L L L S V W A A V L V I L S
BPTC   K Y E A K G L P N F P S G I P F L F W E Q Y L Y L R T S L L L A L A C A L G A V F I A V M V L L L N A W A A V L V T L A
       .  *     .  *   *  .  .   *   *  *  *  *  .  .  *  .     .     *     .  .      .  .       .  .  .  .  .  .

HPTC   L A L M T V E L F G M M G L I G I K L S A V P V V I L I A S V G I G V E F T V H V A L A F L T A I G D K N R R A V L A L
MPTC   L A L M T V E L F G M M G L I G I K L S A V P V V I L I A S V G I G V E F T V H V A L A F L T A I G D K N H R A M L A L
PTC    V L A S L A Q I F G A M T L L G I K L S A I P A V I L I L S V G M M L C F N V L I S L G F M T S V G N R Q R R V Q L S M
BPTC   L A T L V L Q L L G V M A L L G V K L S A M P P V L L V L A I G R G V H F T V H L C L G F V T S I G C K R R A S L A L
            *                    *   *  *    *       *             *       *    *    *     *     *     *                *

HPTC   E H M F A P V L D G A V S T L L G V L M L A G S E F D F I V R Y F F A V L A I L T I L G V L N G L V L L P V L L S F F G
MPTC   E H M F A P V L D G A V S T L L G V L M L A G S E F D F I V R Y F F A V L A I L T V L G V L N G L V L L P V L L S F F G
PTC    Q M S L G P L V H G M L T S G V A V F M L S T S P F E F V I R H F C W L L L V V L C V G A C N S L L V F P I L L S M V G
BPTC   E S V L A P V V H G A L A A A L A A S M L A A S E F G F V A R L F L R L L L A L V F L G L I D G L L F F P I V L S I L G
            *  .  .     .       .   .   .  .         *  .        . .          .  .         *   .        .  .   .  *  *

HPTC   P Y P E V S P A N G L N R L P T P S E P P P S V V R F A M P P G H T H S G S D S S D S E Y S S Q T T V S G L S E - E L
MPTC   P C P E V S P A N G L N R L P T P S P E P P S V V R F A V P P G H T N N G S D S S D S E Y S S Q T T V S G I S E - E L
PTC    P E A E L V P L E H P D R I S T P S P L P V R S S K R S G K S Y V V Q G S R S S R G S C Q K S H H H H H K D L N D P S L
BPTC   P A A E V R P I E H P E R L S T P S P K C S P I H P R K S S S S S G G G D K S S R T S - - K S A P R P C - - - - A P S L
       *   .  *  .  *       .  *  *  * *                                                  *      .                      *

HPTC   R H Y E A Q Q G A G G P A H Q V I V E A T E N P V F A H S T V V H P E S R H H P P S N P R Q Q P H L D S G S L P P G R Q
MPTC   R Q Y E A Q Q G A G G P A H Q V I V E A T E N P V F A R S T V V H P D S R H Q P P L T P R Q Q P H L D S G S L S P G R Q
PTC    T T I T E E P Q S W K S S N S S I Q M P N D W T Y Q P R E Q - - R P A S Y A A P P P A Y H K A A A Q Q H H Q H Q G P P T
BPTC   T T I T E E P S S W H S S A H S V Q S S M Q S I V V Q P E V V V E T T T Y N G S D S A S G R S T P T K S S H G G A I T T
                       .  .         .  .         .

HPTC   G Q Q P R R D P P R E G L W P P L Y R P R R D A F E I S T E G H S G P S N R A R W G P R G A R S H N P R N P A S T A M G
MPTC   G Q Q P R R D P P R E G L R P P P Y R P R R D A F E I S T E G H S G P S N R D R S G P R G A R S H N P R N P T S T A M G
PTC    T P P P P F P T A - - - - - - - - - - - - - - - - - - Y P P E L Q S I V V Q P E V T V E T T H S - - - - - - - - - - - D S
BPTC   T K V T A T A N I K V E V V T P S D R K S R R S Y H Y Y D R R R D R D E D R D R D R E R D R D R D R D R D R D R D R
                                                           .

HPTC   S S V P G Y C Q P I T T V T A S A S V T V A V H P P P V P G P G R N P R G G L C P G Y - - - P E T D H G L F E D P H V P
MPTC   S S V P S Y C Q P I T T V T A S A S V T V A V H P P - - P G P G R N P R G G P C P G Y E S Y P E T D H G V F E D P H V P
PTC    N T - - - - - - - - T K V T A T A N I K V E L A M P - - - - - G R A V R S - - - Y N F T S - - - - - - - - - - - - - -
BPTC   D R - - - - - - - - D R E R S R E R D R R D R Y R D - - - - - E R D H R A - - - S P R E N G R D S G H E - - - - - - - -
                                                                       *       * .

HPTC   F H V R C E R R D S K V E V I E L Q D V E C E E R P R G S
```

The identity of ten other clones recovered from the mouse library is not determined. These cDNAs cross-hybridize with mouse ptc sequence, while differing as to their restriction maps. These genes encode a family of proteins related to the patched protein. Alignment of the human and mouse nucleotide sequences, which includes coding and noncoding sequence, reveals 89% identity.

In accordance with the subject invention, mammalian patched genes, including the mouse and human genes, are provided which allow for high level production of the patched protein, which can serve many purposes. The patched protein may be used in a screening for agonists and antagonists, for isolation of its ligand, particularly hedgehog, more particularly Sonic hedgehog, and for assaying for the transcription of the mRNA ptc. The protein or fragments thereof may be used to produce antibodies specific for the protein or specific epitopes of the protein. In addition, the gene may be employed for investigating embryonic development, by screening fetal tissue, preparing transgenic animals to serve as models, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid comprising a ptc coding sequence for a naturally occurring vertebrate patched polypeptide, or allelic variant thereof, wherein the ptc coding sequence hybridizes which binds to a hedgehog polypeptide to the complement of the coding sequence of SEQ ID Nos. 9 or 18 under stringency conditions equivalent to 5× SSC at 60° C.

2. The nucleic acid of claim 1, wherein the ptc coding sequence hybridizes to the complement of the coding sequence of SEQ ID Nos. 9 or 18 under stringency conditions equivalent to 0.1× SSC at 50° C.

3. The nucleic acid of claim 1, or 2, wherein the ptc coding sequence encodes a mammalian patched polypeptide.

4. The nucleic acid of claim 3, wherein the coding sequence encodes a primate patched polypeptide.

5. The nucleic acid of claim 4, wherein the coding sequence encodes a human patched polypeptide.

6. The nucleic acid of claim 1, wherein the amino acid sequence of the ptc polypeptide is identical to SEQ ID No. 10 or 19.

7. The nucleic acid of claim 1, wherein the ptc coding sequence is identical to SEQ ID No. 9 or 18.

8. An isolated nucleic acid comprising a coding sequence for a polypeptide including a hedgehog-binding sequence that binds hedgehog protein and which is encoded by a nucleotide sequence that hybridizes to the complement of the coding sequence of SEQ ID Nos. 9 or 18 under stringency conditions equivalent to 5× SSC at 60° C, wherein the polypeptide retains hedgehog-binding activity.

9. The nucleic acid of claim 8, wherein the hedgehog-binding sequence is encoded by a nucleotide sequence that hybridizes to the complement of the coding sequence of SEQ ID Nos. 9 or 18 under stringency conditions equivalent to 0.1 × SSC at 60° C.

10. The nucleic acid of claim 8, or 9, wherein the hedgehog-binding sequence is from a mammalian patched polypeptide.

11. The nucleic acid of claim 10, wherein the hedgehog-binding sequence is from a primate patched polypeptide.

12. The nucleic acid of claim 11, wherein the hedgehog-binding sequence is from a human patched polypeptide.

13. The nucleic acid of claim 8, wherein the nucleotide sequence encoding the hedgehog-binding sequence is at least 267 base pairs in length.

14. The nucleic acid of claim 8, wherein the nucleotide sequence encoding the hedgehog-binding sequence is at least 345 base pairs in length.

15. The nucleic acid of claim 14, wherein the hedgehog-binding sequence includes at least 3 extracellular loops.

16. The nucleic acid of claim 8, wherein the hedgehog protein is selected from the group consisting of Sonic hedgehog, Indian hedgehog, and Desert hedgehog.

17. A nucleic acid comprising: (i) a coding sequence from a naturally occurring vertebrate ptc gene or allelic variant thereof, which coding sequence (a) hybridizes to the complement of the coding sequence of SEQ ID Nos. 9 or 18 under stringency conditions equivalent to 5× SSC at 60° C.

and (b) encodes a polypeptide that binds hedgehog proteins, and (ii) a heterologous transcriptional initiation region controlling the transcription of the coding sequence.

18. The nucleic acid of claim 1, or 8, further comprising a heterologous transcription initiation region that controls transcription of the coding sequence.

19. The nucleic acid of claim 18, wherein the transcription initiation region is inducible.

20. The nucleic acid of claim 18, wherein the transcription initiation region includes a promoter.

21. A nucleic acid comprising: (i) a coding sequence for a polypeptide including a hedgehog-binding sequence that (a) binds hedgehog protein and (b) is encoded by a nucleotide sequence that hybridizes to the complement of the coding sequence of SEQ ID Nos. 9 or 18 under stringency conditions equivalent to 5× SSC at 60° C., and (ii) a heterologous transcriptional initiation region controlling the transcription of the coding sequence, wherein the polypeptide retains hedgehog-binding activity.

22. The nucleic acid of claim 17, wherein the coding sequence hybridizes to the complement of the coding sequence of SEQ ID Nos. 9 or 18 under stringency conditions equivalent to 0.1× SSC at 50° C.

23. The nucleic acid of claim 17, wherein the amino acid sequence of the ptc polypeptide is identical to SEQ ID No. 10 or19.

24. The nucleic acid of claim 17, wherein the coding sequence is identical to SEQ ID No. 9 or 18.

25. The nucleic acid of claim 21, wherein the hedgehog-binding sequence is encoded by a nucleotide sequence that hybridizes to the complement of the coding sequence of SEQ ID Nos. 9 or 18 under stringency conditions equivalent to 0.1× SSC at 60° C.

26. The nucleic acid of claim 21, wherein the coding sequence encodes a mammalian patched polypeptide.

27. The nucleic acid of claim 26, wherein the coding sequence encodes a primate patched polypeptide.

28. The nucleic acid of claim 27, wherein the coding sequence encodes a human patched polypeptide.

29. A cell comprising and expressing the nucleic acid of claim 1, 8, 17, or 21.

30. The cell of claim 29, which cell is a eukaryotic cell.

31. The cell of claim 30, which cell is mammalian cell.

32. The nucleic acid of claim 13, wherein the nucleotide sequence encoding the hedgehog-binding sequence is at least 1 Kbp in length.

* * * * *

UNITED STATES PATENT AND TRADEMARK OFFICE
CERTIFICATE OF CORRECTION

PATENT NO.   : 5,837,538
DATED        : November 17, 1998
INVENTOR(S)  : Matthew P. Scott, Lisa V. Goodrich and Ronald L. Johnson It is certified that error appears in the above-identified patent and that said Letters Patent is hereby corrected as shown below:

Column 69,
Line 64, insert -- which binds to a hedgehog polypeptide, -- following "or allelic variant thereof,".
Line 65-Column 70, line 61, delete "which binds to a hedgehog polypeptide" following "hybridizes".

Column 71,
Line 3, delete "," following "1".
Line 27, delete "," following "8".

Signed and Sealed this

Twenty-fourth Day of September, 2002

Attest:

Attesting Officer

JAMES E. ROGAN
Director of the United States Patent and Trademark Office